US008891841B2

(12) United States Patent
Schultz et al.

(10) Patent No.: US 8,891,841 B2
(45) Date of Patent: Nov. 18, 2014

(54) MOBILE DERMATOLOGY COLLECTION AND ANALYSIS SYSTEM

(75) Inventors: Paul T. Schultz, Colorado Springs, CO (US); Robert A. Sartini, Colorado Springs, CO (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 193 days.

(21) Appl. No.: 13/487,786

(22) Filed: Jun. 4, 2012

(65) Prior Publication Data

US 2013/0322711 A1 Dec. 5, 2013

(51) Int. Cl.
*G06K 9/00* (2006.01)
(52) U.S. Cl.
USPC ............................................. 382/128
(58) Field of Classification Search
None
See application file for complete search history.

(56) References Cited

U.S. PATENT DOCUMENTS

| 2007/0110290 | A1* | 5/2007 | Chang et al. | 382/128 |
| 2009/0245603 | A1* | 10/2009 | Koruga et al. | 382/128 |
| 2011/0103660 | A1* | 5/2011 | Butler et al. | 382/128 |
| 2011/0123071 | A1* | 5/2011 | Shah et al. | 382/118 |
| 2012/0051605 | A1* | 3/2012 | Nagar et al. | 382/124 |

* cited by examiner

*Primary Examiner* — Bhavesh Mehta
*Assistant Examiner* — Siamak Harandi

(57) ABSTRACT

A method, performed by a mobile communication device, may include obtaining one or more images, extracting one or more features from the one or more images, and determining a dermatological classification for the obtained one or more images based on the extracted one or more images and based on a dermatological analysis model. The method may further include determining a recommendation based on the determined dermatological classification and providing information about the determined dermatological classification along with the recommendation to a user of the mobile communication device.

20 Claims, 21 Drawing Sheets

MOBILE DERMATOLOGY COLLECTION AND ANALYSIS SYSTEM

BACKGROUND INFORMATION

A person may experience a health concern and visit a physician to receive a diagnosis and treatment for the health concern. However, the person may not be able to a visit a physician for some time and may desire immediate information about the health concerns. Furthermore, some health concerns may be minor and may not require medical attention from a medical professional. For example, a person may develop a skin rash and may desire information about the skin rash without having to visit a physician.

DETAILED DESCRIPTION OF PREFERRED EMBODIMENTS

Figure 1:
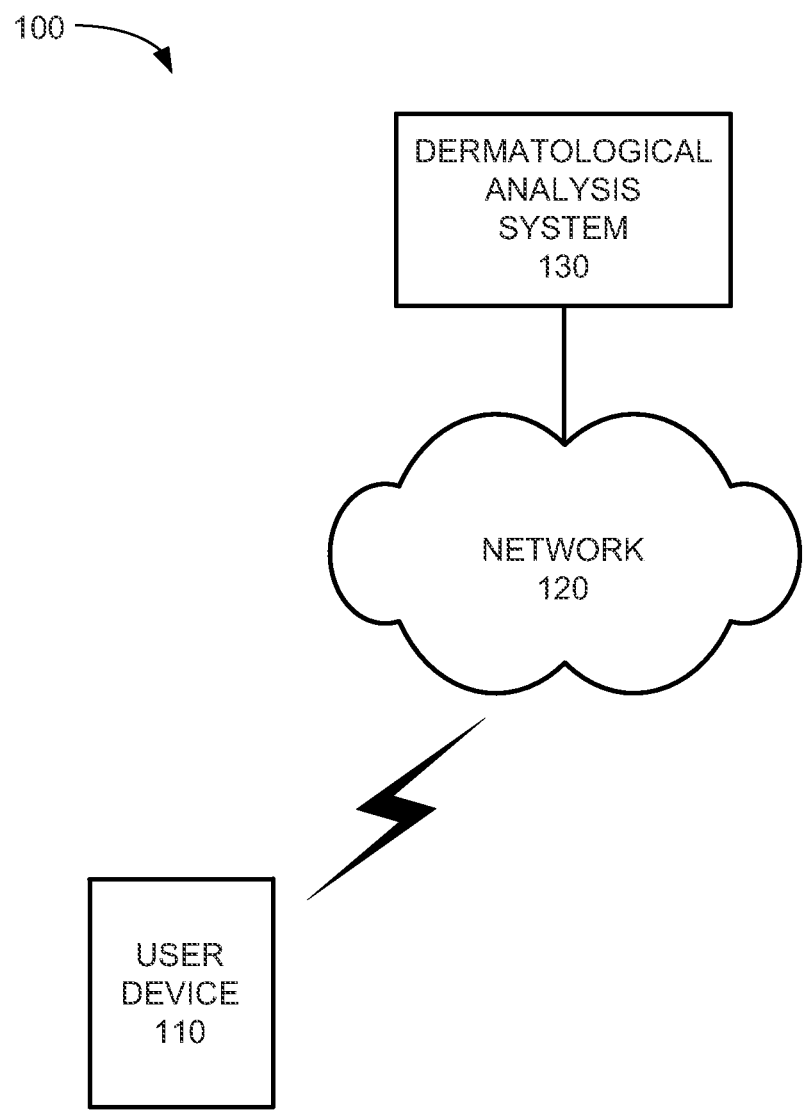
FIG. 1 is a diagram of an exemplary environment according to an implementation described herein.

The following detailed description refers to the accompanying drawings. The same reference numbers in different drawings identify the same or similar elements.

An implementation described herein relates to systems and methods for performing a dermatological analysis using one or more images obtained via a mobile communication device. For example, one or more images may be obtained by the mobile communication device and processed to obtain a dermatological classification and/or recommendation.

Dermatological classification may be based on a dermatological analysis model. The dermatological analysis model may be developed by obtaining a set of images and obtaining labels for the set of images. For example, trained dermatologists may label the set of images with dermatological classifications. Features may be extracted from the images and each dermatological classification may be assigned a set of weights for a set of features based on the features extracted from the images. An image may subsequently be classified by applying the set of weights to features ex acted from the image to determine a dermatological classification for the image.

In one implementation, the user of the mobile communication device may capture an image of an area of the user's skin and may send the image to an address associated with a dermatological analysis system with a request for a dermatological analysis and/or recommendation. The dermatological analysis system may extract features from the image and may apply a dermatological analysis model to classify the image into a dermatological classification. The dermatological classification may correspond to a particular skin disease or condition. The dermatological analysis system may send the determined dermatological classification to the mobile communication device along with a recommendation relating to an action and/or treatment associated with the determined dermatological classification (e.g., applying an over-the-counter medication if the condition is not serious, recommending a visit to a doctor if the condition is serious, etc.).

In another implementation, the mobile communication device may include devices and/or functionality configured to provide dermatological analysis. For example, the mobile communication device may include multiple cameras and/or light sources that may enable the user to obtain more information about a skin condition, such as one or more of an infrared light camera, an ultraviolet light camera, a polarized light camera, a camera with a macrophotography lens, a dermatoscope, and/or another type of camera. Furthermore, the mobile communication device may be configured to instruct the user to obtain multiple images of an area of skin. For example, the mobile communication device may instruct the user to capture images at different camera angles, at different magnifications, and/or using different illumination configurations.

Moreover, the mobile communication device may be configured to provide a dermatological questionnaire to the user to obtain more information about the user's condition and may include answers received from the user in the dermatological analysis. Furthermore, the mobile communication device may perform some or all image processing to determine the dermatological classification and/or may fork some of the image processing to a dermatological analysis server.

In one implementation, features may be extracted from images and a dermatological analysis model may be applied to the extracted features to determine a dermatological classification. In another implementation, images may be analyzed to identify lesions, the identified lesions may be analyzed to determine attributes associated with the lesions, and the identified lesions may be classified based on the determined attributes. A dermatological classification may be determined based on the classified lesions.

FIG. 1 is a of an exemplary environment 100 in which the systems and/or methods described herein may be implemented. As shown in FIG. 1, environment 100 may include a user device 110, a network 120, and a dermatological analysis system 130. While FIG. 1 shows a single user device 110, a single network 120, and a single dermatological analysis system 130 for illustrative purposes, in practice, environment 100 may include multiple user devices 110, multiple networks 120, and/or multiple dermatological analysis systems 130.

User device 110 (also referred to herein as mobile communication device 110) may include any portable electronic device with communication functionality, such as, for example, a mobile phone, a smart phone, a tablet computer, a laptop computer, a personal digital assistant or another type of portable communication device. User device 110 may be configured to capture an image of the user's skin using one or more camera and/or illumination devices. User device 110 may send information associated with a captured image and/or a completed questionnaire to dermatological analysis system 130, and may receive information associated with an analysis corresponding to the captured image and/or completed questionnaire from dermatological analysis system 130. User device 110 may use the received information to provide a dermatological analysis and/or recommendation to the user. Alternatively, user device 110 may perform some or all of the dermatological analysis.

Network 120 may enable user device 110 to communicate with dermatological analysis system 130. Network 120 may include one or more wired and/or wireless networks. For example, network 120 may include a cellular network, the Public Land Mobile Network (PLMN), a second generation (2G) network, a third generation (3G) network, a fourth generation (4G) network (e.g., a long term evolution (LIE) network), a fifth generation (5G) network, a code division multiple access (CDMA) network, a global system for mobile communications (GSM) network, a general packet radio services (GPRS) network, a Wi-Fi network, an Ethernet network, a combination of the above networks, and/or another type of wireless network. Additionally, or alternatively, network 120 may include a local area network (LAN), a wide area network (WAN), a metropolitan area network (MAN), an ad hoc network, an intranet, the Internet, a fiber optic-based network (e.g., a fiber optic service network), a satellite network, a television network, and/or a combination of these or other types of networks.

Dermatological analysis system 130 may include one or more devices, such as a server device, that may receive one or more images from user device 110, and/or additional information, such as answers to a dermatological questionnaire, and may perform a dermatological analysis based on the received images and/or information using a dermatological analysis model. In one implementation, dermatological analysis system 130 may send information relating to a dermatological classification and/or recommendation to user device 110. In another implementation, dermatological analysis system 130 may perform image processing to extract features from the received one or more images and may send information about the extracted features to user device 110. Thus, user device 110 may offload computationally expensive image processing to dermatological analysis system 130.

Although FIG. 1 shows exemplary components of environment 100, in other implementations, environment 100 may include fewer components, different components, differently arranged components, or additional components than depicted in FIG. 1. Additionally or alternatively, one or more components of environment 100 may perform functions described as being performed by one or more other components of environment 100.

Figure 2:
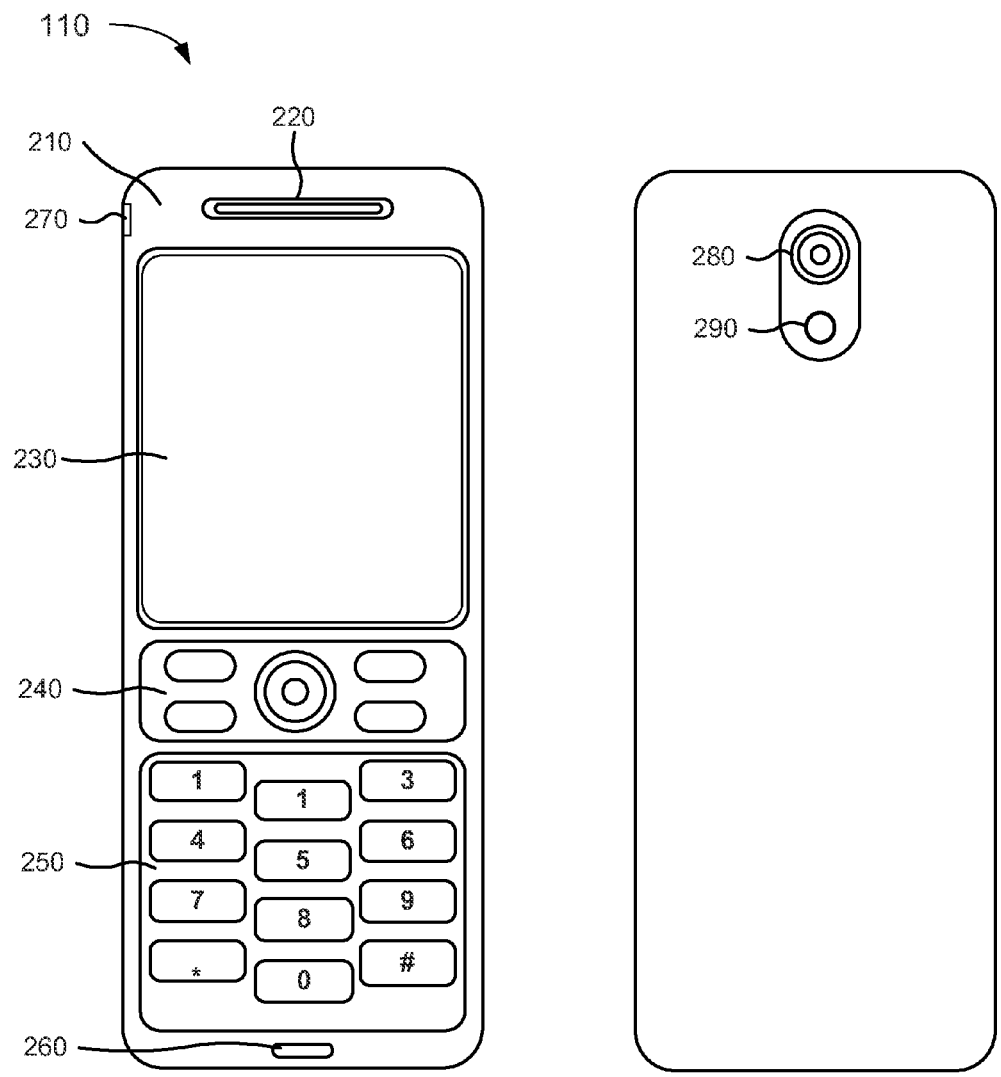
FIG. 2 is a diagram of a first exemplary user device according to an implementation described herein.

FIG. 2 is a diagram of a first exemplary user device 110 according to an implementation described herein. As shown in FIG. 2, user device 110 may include a housing 210, a speaker 220, a display 230, a control buttons 240, a keypad 250, a microphone 260, an audio/visual (A/V) interface port 270, a camera 280, and an illumination device 290. Housing 210 may protect the components of user device 110 from outside or environmental elements. Speaker 220 may provide audible information to a user of user device 110.

Display 230 may provide visual information to the user. For example, display 230 may provide information regarding incoming or outgoing telephone calls and/or incoming or outgoing electronic mail (e-mail), instant messages, short message service (SMS) messages, etc. Control buttons 240 may permit the user to interact with user device 110 to cause user device 110 to perform one or more operations, such as place a telephone call, play various media, etc. For example, control buttons 240 may include a dial button, hang up button, play/pause button, etc. Keypad 250 may include a standard telephone keypad. Microphone 260 may receive audible information from the user. A/V interface port 270 may include a you or receptacle for receiving a terminal operatively connected to an external device, such as a hands free heads headphones, an external display, a home or car audio system, etc.

Camera 280 may enable the user of user device 110 to capture an image. For example, camera 280 may include a charge-coupled device, a complementary metal-oxide-semiconductor (CMOS) active pixel sensor, and/or another type of sensor. Illumination device 290 may include a light source for providing a flash during image capture by camera 280. For example, illumination device 290 may include one or more light emitting diodes (LEDs) and/or another type of tight generating device.

Figure 3:
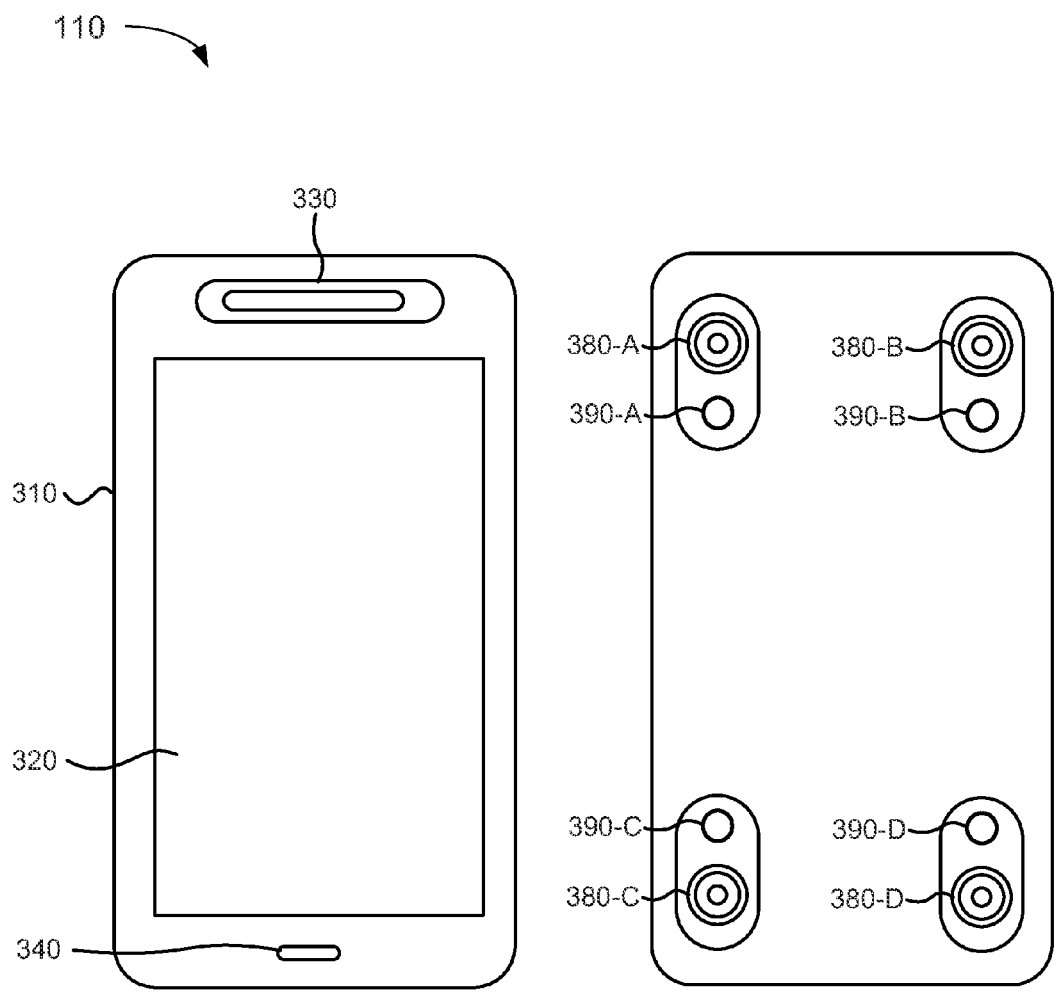
FIG. 3 is a diagram of a second exemplary user device according to an implementation described herein.

FIG. 3 is a diagram of a second exemplary user device 110 according to an implementation described herein. As shown in FIG. 3, user device 110 may include a housing 310, a touch screen 320, a speaker 330, a microphone 340, cameras 380-A through 380-D (referred to herein collectively as "cameras 380" and individually as "camera 380"), and illumination devices 390-A through 390-D (referred to herein collectively as "illumination devices 390" and individually as "illumination device 390"). User device 110 may include fewer or additional cameras 380 and/or illumination devices 390.

Housing 310 may protect the components of user device 110 from outside or environmental elements. Touch screen 320 may provide visual information to the user and may receive input information from the user. Touch screen 320 may be operated using a stylus (not shown in FIG. 3) that may be provided with user device 110 when user device 110 is purchased. Speaker 330 may provide audible information to a user of user device 110. Microphone 340 may receive audible information from the user.

Cameras 380 may include the same types of camera devices and/or different types of camera devices. Illumination devices 390 may include the same types of illumination devices and/or different types of illumination devices.

As an example, one or more of cameras 380 may include a visible light camera (e.g., a camera that includes a charge-coupled sensor, a complementary metal-oxide-semiconductor (CMOS) active pixel sensor, and/or another type of sensor) and one or more of illumination devices 390 may include a visible light source (e.g., an LED light source). As another example, one or more of cameras 380 may include an infrared camera 380 and illumination device 390 may include an infrared light source. As yet another example, one or more of cameras 380 may include a controllable infrared blocker that may enable respective cameras 380 to be configured to function as both a visible light camera and an infrared camera.

As yet another example, one or more of cameras 380 may include a UV camera and one or more illumination devices 390 may include a UV light source. As yet another example, one or more of cameras 380 may include a controllable polarizing filter and/or one or more of illumination devices 390 may include a controllable polarized light source. As yet another example, one or more of cameras 380 may include a camera with a macrophotography lens. As yet another example, one or more of cameras 380 and one or more of illumination devices 390 may correspond to a dermatoscope.

Figure 4:
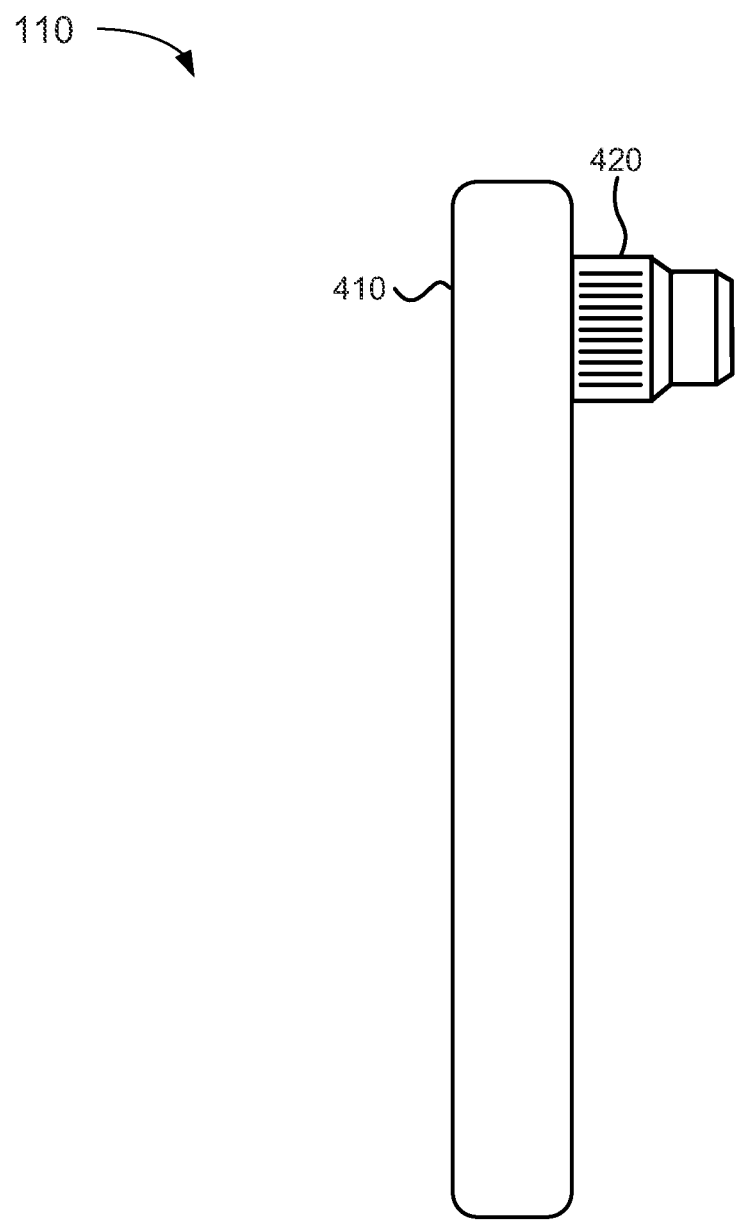
FIG. 4 is a diagram of a third exemplary user device according to an implementation described herein.

FIG. 4 is a diagram of a third exemplary user device 110 according to an implementation described herein. As shown in FIG. 4, user device 110 may include a mobile communication device 410 coupled to a dermatoscope 420. Dermatoscope 420 may be detachable from mobile communication device 410 and mobile communication device 410 may include an adapter (not shown in FIG. 4) to secure dermatoscope 420 to camera 380. Dermatoscope 420 may include, for example, a polarized light source to cancel out skin reflections and a magnifying lens that may magnify light received by camera 380.

Although FIGS. 2-4 show exemplary components of user device 110, in other implementations, user device 110 may include fewer components, different components, differently arranged components, or additional components than depicted in FIGS. 2-4. Additionally or alternatively, one or more components of user device 110 may perform functions described as being performed by one or more other components of user device 110.

Figure 5:
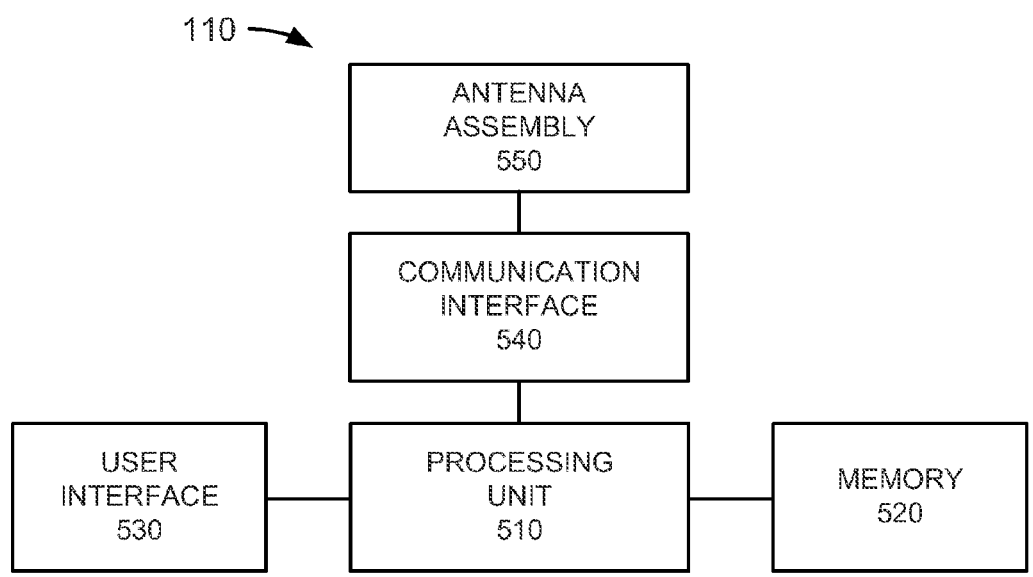
FIG. 5 is a diagram illustrating exemplary components of the user device of FIG. 1.

FIG. 5 is a diagram illustrating exemplary components of user device 110 according to an implementation described herein. As shown in FIG. 5, user device 110 may include a processing unit 510, a memory 520, a user interface 530, a communication interface 540, and an antenna assembly 550.

Processing unit 510 may include one or more processors, microprocessors, application specific integrated circuits (ASICs), field programmable gate arrays (FPGAs), or other processing logic. Processing unit 510 may control operation of user device 110 and the components of user device 110.

Memory 520 may include a random access memory (RAM) or another type of dynamic storage device, a read only memory (ROM) or another type of static storage device, a removable memory card, and/or another type of memory to store data and instructions that may be used by processing unit 510.

User interface 530 may include mechanisms for inputting information to user device 110 and/or for outputting information from user device 110. Examples of input and output mechanisms might include a speaker to receive electrical signals and output audio signals; a camera lens to receive image and/or video signals and output electrical signals; a microphone to receive audio signals and output electrical signals; buttons (e.g., a joystick, control buttons, a keyboard, or keys of a keypad) and/or a touchscreen to permit data and control commands to be input into user device 110; a display, such as a liquid crystal display (LCD), to output visual information; a vibrator to cause user device 110 to vibrate and/or provide detailed haptic feedback to the user; a stylus to enable a user to draw or write on a touch screen; and/or any other type of input or output device.

Communication interface 540 may include a transceiver that enables user device 110 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 540 may include a transmitter that converts baseband signals to radio frequency (RF) signals and/or a receiver that converts RF signals to baseband signals. Communication interface 540 may be coupled to antenna assembly 550 for transmitting and receiving RF signals.

Communication interface 540 may also include a logical component that includes input and/or output ports, input and/or output systems, and/or other input and output components that facilitate the transmission of data to other devices. For example, communication interface 540 may include a network interface card (e.g., Ethernet card) for wired communications and/or a wireless network interface (e.g., a WiFi) card for wireless communications. Communication interface 540 may also include a universal serial bus (USB) port for communications over a cable, a Bluetooth™ wireless interface, a Zigbee wireless interface, a Z-Wave wireless interface, a radio-frequency identification (RFID) interface, a near-field communications (NFC) wireless interface, and/or any other type of interface that converts data from one form to another form.

Antenna assembly 550 may include one or more antennas to transmit and/or receive RF signals over the air. Antenna assembly 550 may, for example, receive RF signals from communication interface 540 and transmit the signals over the air and receive RF signals over the air and provide them to communication interface 540.

As described herein, user device 110 may perform certain operations in response to processing unit 510 executing software instructions contained in a computer-readable medium, such as memory 520. A computer-readable medium may be defined as a non-transitory memory device. A memory device may include memory space within a single physical memory device or spread across multiple physical memory devices. The software instructions may be read into memory 520 from another computer-readable medium or from another device via communication interface 540. The software instructions contained in memory 520 may cause processing unit 510 to perform processes that will be described later. Alternatively, hardwired circuitry may be used in place of, or in combination with, software instructions to implement processes described herein. Thus, implementations described herein are not limited to any specific combination of hardware circuitry and software.

Although FIG. 5 shows example components of user device 110, in other implementations, user device 110 may include fewer components, different components, differently arranged components, or additional components than depicted in FIG. 5. Additionally or alternatively, one or more components of user device 110 may perform the tasks described as being performed by one or more other components of user device 110.

Figure 6:
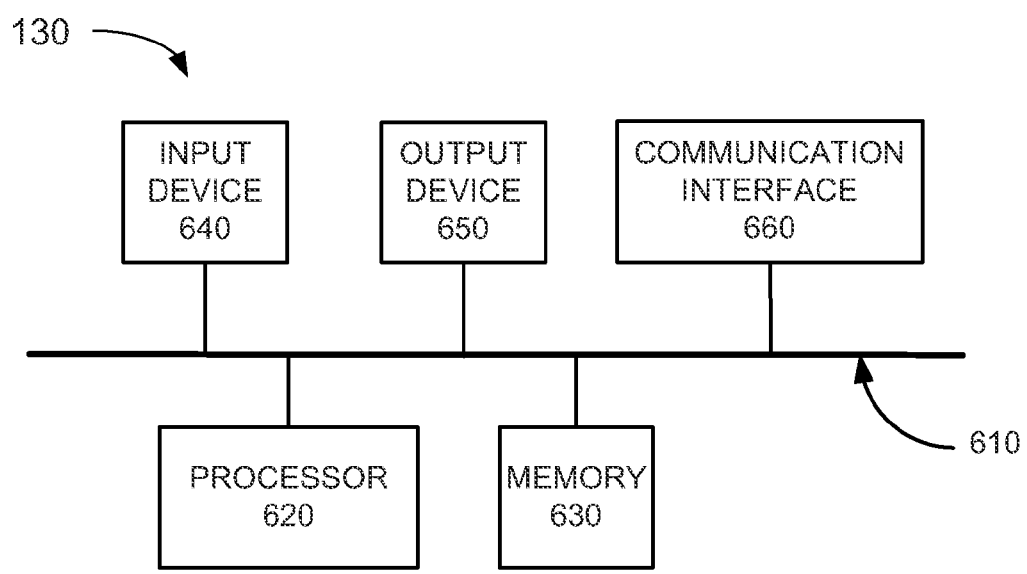
FIG. 6 is a diagram illustrating exemplary components of the dermatological analysis system of FIG. 1.

FIG. 6 is a diagram illustrating exemplary components of dermatological analysis system 130 according to an implementation described herein. As shown in FIG. 6, dermatological analysis system 130 may include a bus 610, a processor 620, a memory 630, an input device 640, an output device 650, and a communication interface 660.

Bus 610 may include a path that permits communication among the components of dermatological analysis system 130. Processor 620 may include any type of single-core processor, multi-core processor, microprocessor, latch-based processor, and/or processing logic (or families of processors, microprocessors, and/or processing logics) that interprets and executes instructions. In other embodiments, processor 620 may include an application-specific integrated circuit (ASIC), a field-programmable gate array (FPGA), and/or another type of integrated circuit or processing logic.

Memory 630 may include any type of dynamic storage device that may store information and/or instructions, for execution by processor 620, and/or any type of non-volatile storage device that may store information for use by processor 620. For example, memory 630 may include a random access memory (RAM) or another type of dynamic storage device, a read-only memory (ROM) device or another type of static storage device, a content addressable memory (CAM), a magnetic and/or optical recording memory device and its corresponding drive a hard disk drive, optical drive, etc.), and/or a removable form of memory, such as a flash memory.

Input device 640 may allow an operator to input information into dermatological analysis system 130. Input device 640 may include, for example, a keyboard, a mouse, a pen, a microphone, a remote control, an audio capture device, an image and/or video capture device, a touch-screen display, a stylus, and/or another type of input device. In some embodiments, dermatological analysis system 130 may be managed remotely and may not include input device 640. In other words, dermatological analysis system 130 may be "headless" and may not include a keyboard, for example.

Output device 650 may output information to an operator of dermatological analysis system 130. Output device 650 may include a display, a printer, a speaker, haptics, and/or another type of output device. For example, dermatological analysis system 130 may include a display, which may include a liquid-crystal display (LCD) for displaying content to the customer. In some embodiments, dermatological analysis system 130 may be managed remotely and may not include output device 650. In other words, dermatological analysis system 130 may be "headless" and may not include a display, for example.

Communication interface 660 may include a transceiver that enables dermatological analysis system 130 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 660 may include a transmitter that converts baseband signals to radio frequency (RF) signals and/or a receiver that converts RF signals to baseband signals. Communication interface 660 may be coupled to an antenna for transmitting and receiving RF signals.

Communication interface 660 may include a logical component that includes input and/or output ports, input and/or output systems, and/or other input and output components that facilitate the transmission of data to other devices. For example, communication interface 660 may include a network interface card (e.g., Ethernet card) for wired communications and/or a wireless network interface (e.g., a WiFi) card for wireless communications. Communication interface 660 may also include a universal serial bus (USB) port for communications over a cable, a Bluetooth™ wireless interface, a Zigbee wireless interface, a Z-Wave wireless interface, a radio-frequency identification (RFID) interface, a near-field communications (NFC) wireless interface, and/or any other type of interface that converts data from one form to another form.

As will be described in detail below, dermatological analysis system 130 may perform certain operations relating to performing dermatological analysis with respect to one or more images, a questionnaire, and/or associated context, received via user device 110 and providing a dermatological analysis and/or recommendation to user device 110. Dermatological analysis system 130 may perform these operations in response to processor 620 executing software instructions contained in a computer-readable medium, such as memory 630. A computer-readable medium may be defined as a non-transitory memory device. A memory device may be implemented within a single physical memory device or spread across multiple physical memory devices. The software instructions may be read into memory 630 from another computer-readable medium or from another device. The software instructions contained in memory 630 may cause processor 620 to perform processes described herein. Alternatively, hardwired circuitry may be used in place of, or in combination with, software instructions to implement processes described herein. Thus, implementations described herein are not limited to any specific combination of hardware circuitry and software.

Although FIG. 6 shows exemplary components of dermatological analysis system 130, in other implementations, dermatological analysis system 130 may include fewer components, different components, additional components, or differently arranged components than depicted in FIG. 6. Additionally or alternatively, one or more components of dermatological analysis system 130 may perform one or more tasks described as being performed by one or more other components of dermatological analysis system 130.

Figure 7:
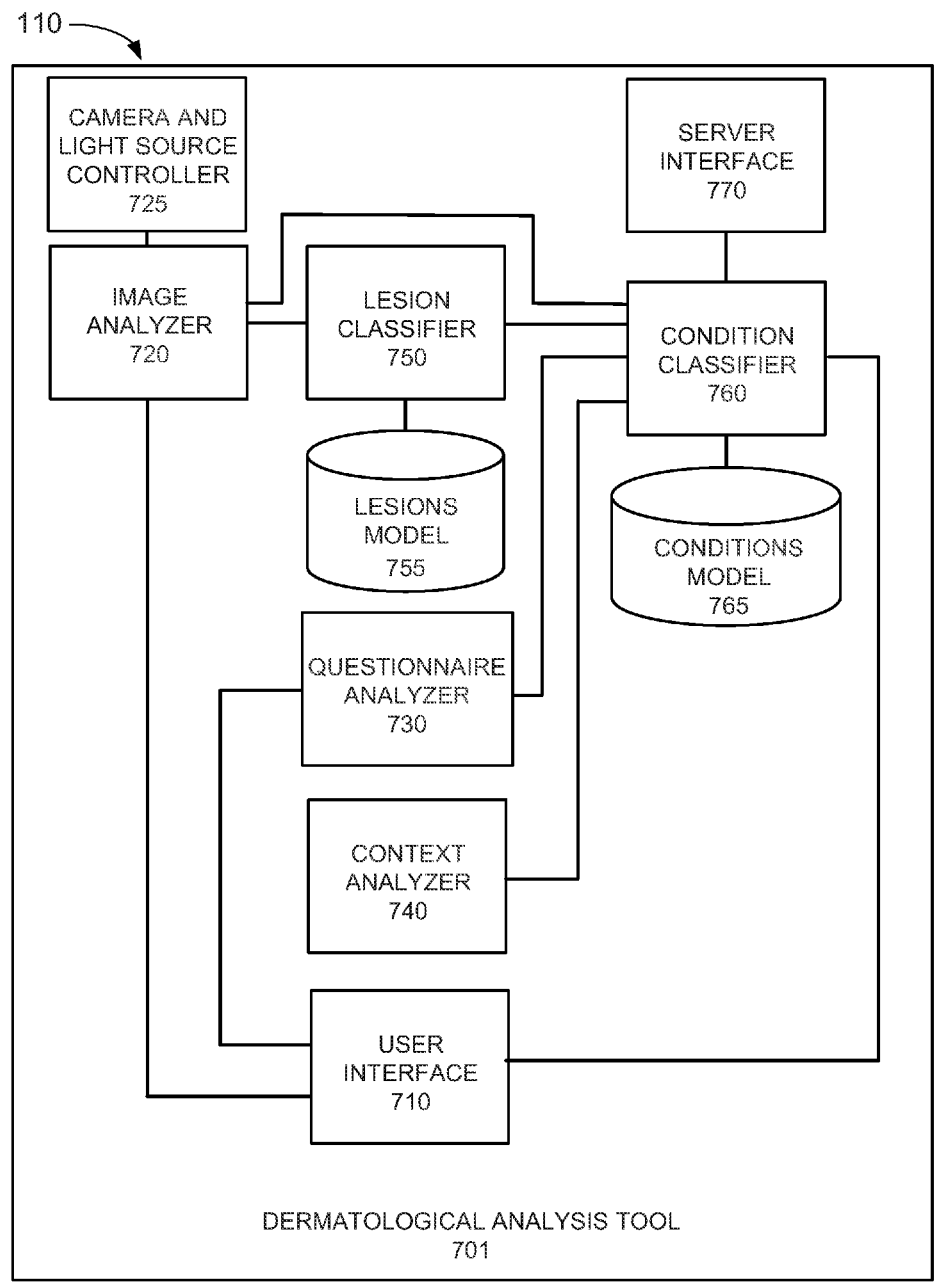
FIG. 7 is a diagram illustrating exemplary functional components of the user device of FIG. 1.

FIG. 7 is a of exemplary functional components of user device 110. The functional components of user device 110 may be implemented, for example, via processing unit 510 executing instructions from memory 520. Alternatively, some or all of the functionality of user device 110 may be hardwired. As shown in FIG. 7, user device 110 may include a dermatological analysis tool 701. Dermatological analysis tool 701 may perform dermatological analysis on one or more images and/or other related information obtained by user device 110. Dermatological analysis tool 701 may include a user interface 710, an image analyzer 720, a camera and light source controller 725, a questionnaire analyzer 730, a context analyzer 740, a lesion classifier 750, a lesions model database 755, a condition classifier 760, a conditions model database 765, and a server interface 770.

User interface 710 may receive input from the user of user device 110 and/or may provide output to the user. For example, user interface 710 may display instructions to user to capture an image and/or fill out a questionnaire. As another example, user interface 710 may receive answers to a questionnaire from the user. As yet another example, user interface 710 may provide results of a dermatological analysis and/or a recommendation to the user.

Image analyzer 720 may analyze an image of an area of the user's skin. For example, image analyzer 720 may determine whether a captured image satisfies one or more criteria, such as a sharpness criterion, an illumination level criterion, a contrast criterion, and/or another type of criterion. If an image does not satisfy the one or more criteria, image analyzer 720 may instruct the user, via user interface 710, to re-capture the image.

Furthermore, image analyzer 720 may process an image to extract one or more features from the image. In one implementation, the extracted features may correspond to features associated with images that were used to generate a dermatological analysis model. For example, a feature may correspond to a particular edge in a particular location, a particular color histogram of a particular region of an image, a particular shape, a particular distribution of shapes, and/or any other feature that may be extracted from an image using a feature extraction algorithm. In another implementation, the extracted features may be associated with particular skin lesions. A skin lesion may correspond to an area of skin that differs in one or more attributes from healthy or normal skin.

Camera and light source controller 725 may control cameras 380 and illumination devices 390 (or camera 280 and illumination device 290). For example, camera and light source controller 725 may determine a sequence of images that are to be captured and may control cameras 380 and illumination devices 390 to capture the sequence of images (e.g., a visible light image followed by an infrared image, a first image at a first magnification and a second image at a second magnification, etc.).

Questionnaire analyzer 730 may analyze answers received from the user in connection with a dermatological questionnaire provided to the user. For example, questionnaire analyzer 730 may convert the answers received from the user into a feature vector that may be provided to condition classifier 760.

Context analyzer 740 may determine a context, associated with the user, which may be relevant to a dermatological condition associated with the user. For example, context analyzer 740 may determine current and/or recent weather associated with the user's location and/or may determine events associated with the user's location. Particular weather conditions may be associated with particular skin conditions. For example, dry weather may be associated with skin conditions exacerbated by dryness. Furthermore, particular events may be associated with particular skin conditions. For example, an industrial accident may be associated with particular skin conditions. The context information may be obtained, by for example, using a search engine to search the Internet for documents matching a particular search term or search phrase. Additionally or alternatively, context information may be obtained from a sensor included in user device 110, such as, for example, a GPS sensor, a temperature sensor, a barometric a pressure sensor, a light sensor, and/or another type of sensor. Context analyzer 740 may convert obtained context information into a feature vector that may be provided to condition classifier 760.

Lesion classifier 750 may obtain information from image analyzer 720 about a particular area of an image along with a feature vector associated with the particular area. Lesion classifier 750 convert the feature vector into a set of one or more attributes and may use the set of one or more attributes to classify the particular area into a lesion classification. Examples of attributes that may be used to classify a lesion may include color, size, shape, elevation, texture, distribution, and/or another type of attribute. Based on the attribute, a lesion may be classified as, for example, a macule, a papule, a nodule, a pustule, a tumor, a plaque, a vesicle, a bullae, a wheal, and/or another type of lesion. Furthermore, a lesion may be further characterized by a pattern or distribution into, for example, an annular lesion, a clustered lesion, etc.

Lesions model database 755 may store information that relates features to lesions. For example, lesions model database 755 may associate a particular set of features with a particular set of attributes and may associate the particular set of attributes with a lesion classification. The information stored in lesions model database 755 may be obtained from dermatological analysis system 130.

Condition classifier 760 may determine a dermatological classification for a user based on information obtained from one or more images, information obtained from a dermatological questionnaire, and/or context information associated with the user. In one implementation, condition classifier 760 may determine a dermatological classification based on a feature vector extracted from one or more images. In another implementation, condition classifier 760 may determine a dermatological classification based on one or more lesion classifications determined by lesion classifier 750. In one implementation, condition classifier 760 may obtain a feature vector from image analyzer 720. In another implementation, condition classifier 760 may obtain a first set of features for an image from image analyzer 720, may forward the image to dermatological analysis system 130, and may receive a second set of features for the image from dermatological analysis system 130. In yet another implementation, dermatological analysis system 130 may perform feature extraction for the image and may determine a dermatological classification and may send information about the determined dermatological classification to condition classifier 760.

Conditions model database 765 may store information that relates features and/or lesion classifications to dermatological classifications (e.g., eczema, hives, psoriasis, etc). For example, conditions model database 765 may associate a particular set of features with a particular dermatological classification. The information stored in conditions model database 765 may be obtained from dermatological analysis system 130.

Server interface 770 may send information to dermatological analysis system 130 and/or may receive information from dermatological analysis system 130. For example, server interface 770 may send an image to dermatological analysis system 130 for processing and may receive a set of features associated with the image from dermatological a analysis system 130. As another example, server interface 770 may send an image (and/or answers to a questionnaire) to dermatological analysis system 130 for processing and may receive a dermatological classification and/or a recommendation associated with the image. As yet another example, server interface 770 may send an image or series of images (e.g., video, motion JPEG, etc.) and context information (e.g., location, temperature, etc.) to dermatological analysis system 130 for processing and may receive a dermatological classification and/or a recommendation associated with the image or series of images.

Although FIG. 7 shows exemplary functional components of user device 110, in other implementations, user device 110 may include fewer functional components, different functional components, differently arranged functional components, or additional functional components than depicted in FIG. 7. Additionally or alternatively, one or more functional components of user device 110 may perform functions described as being performed by one or more other functional components of user device 110.

Figure 8:
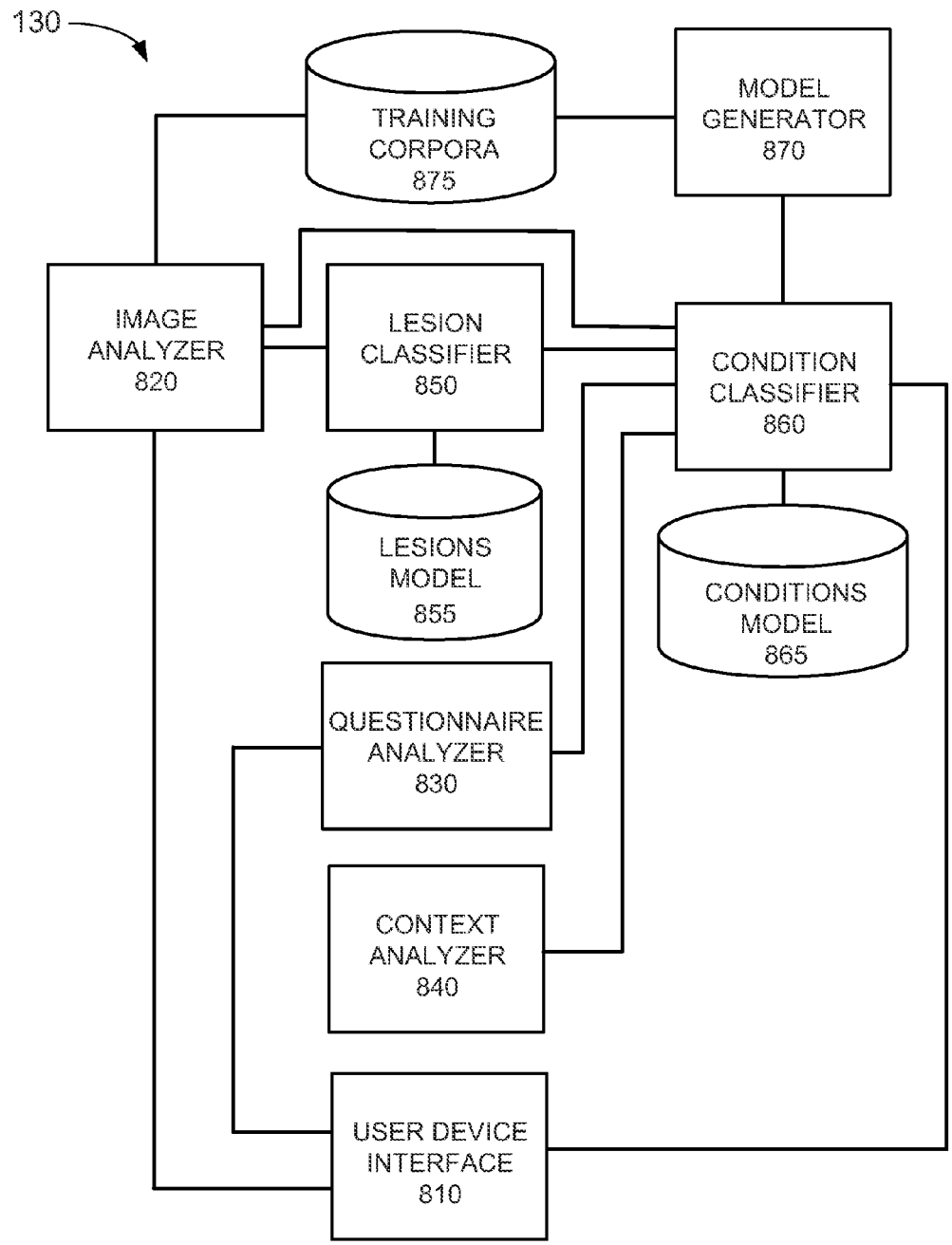
FIG. 8 is a diagram illustrating exemplary functional components of the dermatological analysis system of FIG. 1.

FIG. 8 is a diagram of exemplary functional components of dermatological analysis system 130. The functional components of dermatological analysis system 130 may be implemented, for example, via processor 620 executing instructions from memory 630. Alternatively, some or all of the functionality of dermatological analysis system 130 may be hardwired. As shown in FIG. 8, dermatological analysis system 130 may include a user device interface 810, an image analyzer 820, a questionnaire analyzer 830, a context analyzer 840, a lesion classifier 850, a lesions model database 855, a condition classifier 860, a conditions model database 865, a model generator 870, and a training corpora database 875.

User device interface 810 may interface with user device 110. For example, user interface 810 may provide a dermatological analysis model to user device 110. As another example, user interface 810 may receive an image from user device 110 for processing may send features extracted from the image, a dermatological classification, and/or a recommendation to user device 110. Additionally or alternatively, user device interface 810 may communicate with server interface 770 to afford distributed dermatological data collection and analysis functionality to user of user device 110.

Image analyzer 820 may perform functions similar to the functions described above with respect to image analyzer 720. Questionnaire analyzer 830 may perform functions similar to the functions described above with respect to questionnaire analyzer 730. Context analyzer 840 may perform functions similar to the functions described above with respect to context analyzer 740. Lesion classifier 850 may perform functions similar to the functions described above with respect to lesion classifier 750. Lesions model database 855 may store information similar to the information described above with reference to lesions model database 755. Condition classifier 860 may perform functions similar to the functions described above with respect to condition classifier 760. Conditions model database 865 may store information similar to the information described above with reference to conditions model database 765.

Model generator 870 may generate the information stored in lesions model database 855, conditions model database 865, lesions model database 755, and/or conditions model database 765. For example, model generator 870 may generate a model based on information stored in training corpora database 875. In one implementation, training corpora database 875 may store images of dermatological conditions that have been manually labeled by professional dermatologists. In another implementation, training corpora database 875 may store labeled images of dermatological conditions that have been obtained by searching the Internet. Furthermore, training corpora database 875 may include information that associates dermatological conditions with signs, symptoms, allergens, medications, environmental factors, and/or other information. Model generator 870 may extract features from the images and/or other information stored in training corpora database 875 and may associate the features with particular dermatological conditions.

Although FIG. 8 shows exemplary functional components of dermatological analysis system 130, in other implementations, dermatological analysis system 130 may include fewer functional components, different functional components, differently arranged functional components, or additional functional components than depicted in FIG. 8. Additionally or alternatively, one or more functional components of dermatological analysis system 130 may perform functions described as being performed by one or more other functional components of dermatological analysis system 130.

Figure 9:
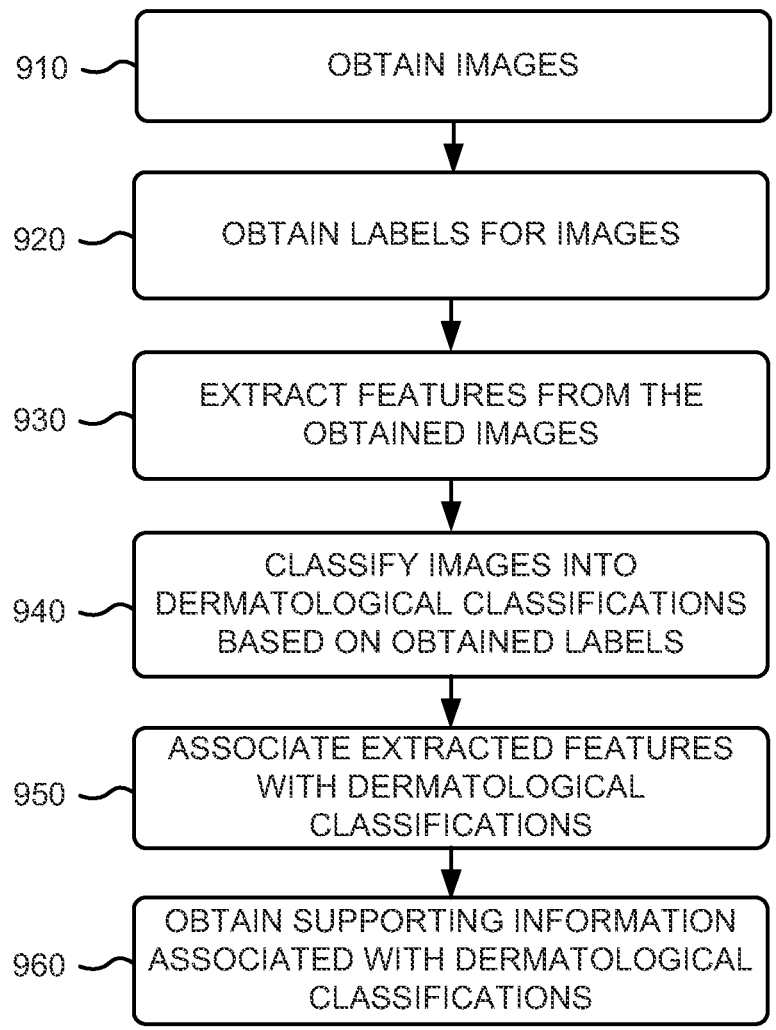
FIG. 9 is a flowchart of an exemplary process for generating a dermatological analysis model according to an implementation described herein.

FIG. 9 is a flowchart of an exemplary process for generating a dermatological analysis model according to an implementation described herein. In one implementation, the process of FIG. 9 may be performed by dermatological analysis system 130. In other implementations, some or all of the process of FIG. 9 may be performed by another device or a group of devices separate from dermatological analysis system 130 and/or including dermatological analysis system 130.

The process of FIG. 9 may include obtaining images (block 910). For example, model generator 870 may access images of dermatological conditions stored in training corpora 875. Labels may be obtained for or assigned to, the images (block 920). In one implementation, the images may manually labeled by dermatology physicians. For example, a dermatologist may identify each image as being associated with a dermatological condition. In another implementation, images may be obtained from the internet by searching the internet and the images may be associated with labels that may include terms indicative of dermatological conditions. Furthermore, the dermatologist may label a particular region in an image as being associated with a particular lesion. Alternatively, an edge detection algorithm, or another kind of feature detection algorithm, may be used to select particular areas of the image to identify lesions in the image and lesions may be associated with dermatological conditions using differential diagnosis information that associates particular types of lesions with particular dermatological conditions.

Features may be extracted from the obtained images (block 930). For example, image analyzer 820 may extract features from the images using one or more feature extraction techniques, such as edge detection techniques, techniques that detect regions of interest, corner detection techniques, blob detection techniques, color histogram techniques, template matching techniques, and/or any other feature detection technique. Feature detection may be applied to an image as a whole. Additionally or alternatively, feature detection may be applied to a region of an image identified as a lesion.

Images may be classified into dermatological categories based on the obtained labels (block 940). For example, model generator 870 may classify an image into a dermatological category based on the label associated with the image. Moreover, model generator 870 may classify a lesion associated with the image into a lesion category based on a label associated with the lesion.

The extracted features may be associated with the dermatological classifications (block 950). For example, model generator 870 may generate a feature vector for each dermatological classification based on the extracted features. The feature vector may include, for example, a weight associated with each feature that may be extracted from an image.

Supporting information associated with the dermatological classifications may be obtained (block 960). For example, information such as signs and symptoms information, allergen information, environmental factors information, location information, and/or other type of information that may be associated with a particular dermatological condition. The supporting information may be provided by a dermatologist. Additionally or alternatively, the information may be obtained by performing a search of the interact using a keyword or phrase associated with a dermatological condition. The supporting information for a dermatological classification may be converted into features and the features may be added to the generated feature vector associated with the dermatological classification.

In one implementation, the generated model may be stored by dermatological analysis system 130 and dermatological analysis may be performed by dermatological analysis system 130. In another implementation, dermatological analysis system 130 may send the generated model to user device 110 and user device 110 may perform the dermatological analysis. In yet another implementation, user device 110 may perform the dermatological analysis in connection with dermatological analysis system 130. For example, dermatological analysis system 130 may perform computationally expensive image processing for user device 110.

Figure 10:
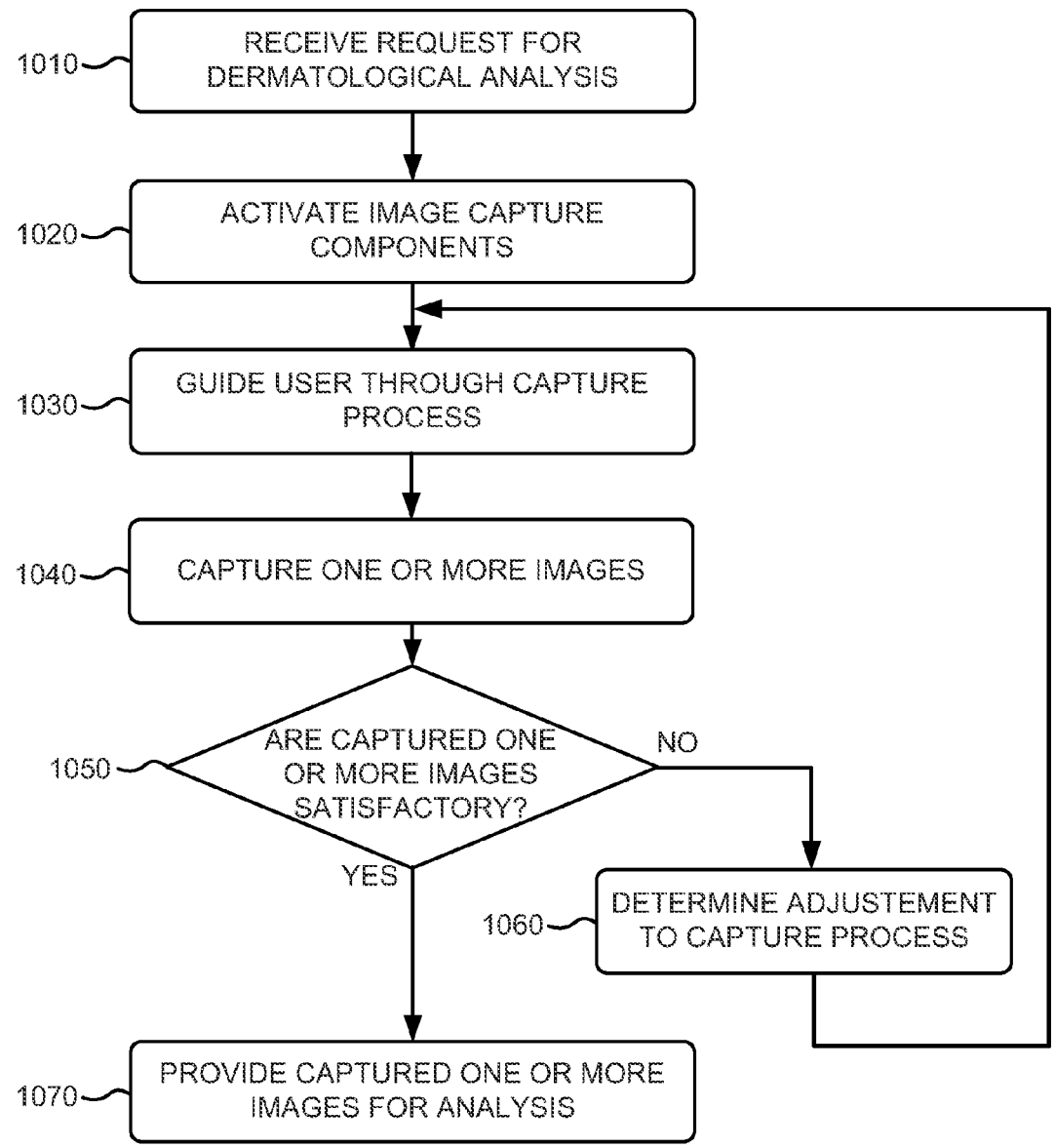
FIG. 10 is a flowchart of an exemplary process for capturing an image according to an implementation described herein.

FIG. 10 is a flowchart of an exemplary process for capturing an image according to an implementation described herein. In one implementation, the process of FIG. 10 may be performed by user device 110. In other implementations, some or all of the process of FIG. 10 may be performed by another device or a group of devices separate from user device 110 and/or including user device 110.

The process of FIG. 10 may include receiving a request for dermatological analysis (block 1010). For example, a user may activate dermatological analysis tool 701 and may activate an option to request a dermatological classification. Image capture components may be activated (block 1020).

For example, camera and light source controller 725 may activate cameras 380 and illumination devices 390 in preparation for capturing images of the user's skin.

The user may be guided through the capture process (block 1030). In one implementation, the user may be guided through a process, for capturing one or more images, which does not depend on the user's particular circumstances. In another implementation, the user's particular circumstances may be taken into account when determining a sequence of images that are to be captured. As an example, a user may be asked to fill out a questionnaire that may include questions about the user's dermatological condition. The user's answers to the questionnaire may be used to estimate a dermatological classification for the user's condition, which may be used to determine a sequence of images that may be required. For example, a first dermatological condition may be determined to require a first set of images (e.g., a visible light image, an infrared light image, etc.) and a second dermatological condition may be determined to require a second set of images (e.g., a first image at a high camera angle, a second image at a low camera angle, etc.). As another example, environmental conditions associated with the user may be used to determine the types of images that are to be captured. For example, the time of day, weather, and/or whether the user is inside or outside may be used to determine light conditions associated with the user and the determined light conditions may be used to determine a sequence of images that are to be captured. The environmental conditions may be determined by querying the user with a set of questions, by obtaining a location associated with user device 110 and by determining the light conditions associated with the location, and/or by using another technique.

As an example, the user may be instructed to hold user device 110 steady at a particular distance and angle from the affected area of skin, while camera and light source controller 725 captures a first image, which may be taken using visible light, followed by a second image, which may be taken using infrared light, UV light, polarized light, and/or another type of light. As another example, a first image may be captured at a first magnification and a second image may be captured at a second magnification. As yet another example, a first image may be captured at a first illumination level and a second image may be captured as a second illumination level.

As yet another example, the user may be instructed to position the camera within a first distance of the affected area of skin to capture a first image, followed by being instructed to position the camera within a second distance (e.g., closer) of the skin to capture a second image. As yet another example, the user may be instructed to position the camera at a first angle to the affected area of skin to capture first image, followed by being instructed to position the camera at a second angle to the affected area of skin to capture a second image. Any combination of the above examples may also be used.

As yet another example, the display of user device 110 may be augment with overlays that may track motion of user device 110 and may provide instructions to train the user to perform a particular task. For example, an overlay may show where to position user device 11) with respect to the affected area of the skin.

Suggest we mention using augmented reality as a possibility for showing user dermatological data gathering procedures. Augmenting the user's display with 2D and or 3D overlays that track with images on the display can be effective in training and informing the user.

A determination may be made as to whether one or more captured images are satisfactory (block 1050). For example, image analyzer 720 may determine whether the captured images satisfy one or more criteria, such as a sharpness criterion, an illumination level criterion, a contrast criterion, a resolution criterion, a magnification criterion, and/or another type of criterion. If it is determined that the captured one or more images are not satisfactory (block 1050—NO), and adjustment to the capture process may be determined (block 1060). For example, camera and tight source controller 725 may adjust the instructions to the user in order to move the captured images in a direction toward satisfying a failed criterion. For example, if a captured image of the area of skin is determined to be too far away, the user may be instructed to move user device 110 closer to the skin for a subsequent attempt. Processing may return to block 1030 to guide the user through the capture process again.

Returning to block 1050, if it is determined that the captured one or more images are satisfactory (block 1050—YES), the captured one or more images may be provided for analysis (block 1070). For example, image analyzer 720 may initiate a feature extraction process for the captured one or more images.

Figure 11:
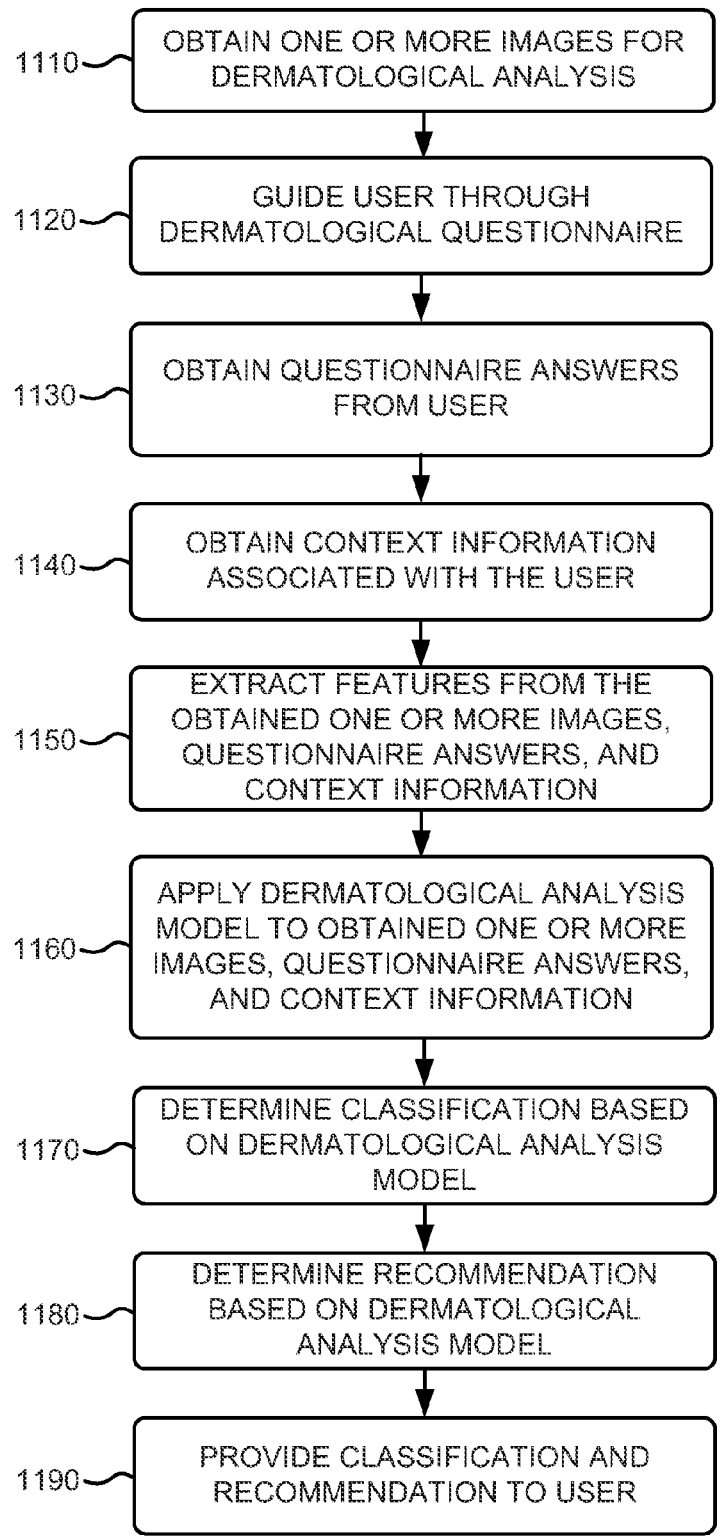
FIG. 11 is a flowchart of an exemplary process for providing a dermatological analysis and recommendation according to an implementation described herein.

FIG. 11 is a flowchart of an exemplary process for providing a dermatological analysis and recommendation according to an implementation described herein. In one implementation, the process of FIG. 11 may be performed by user device 110. In other implementations, some or all of the process of FIG. 11 may be performed by another device or a group of devices separate from user device 110 and/or including user device 110.

The process of FIG. 11 may include obtaining one or more images for dermatological analysis (block 1110). For example, one or more images may be obtained using the process of FIG. 10 described above. The user may be guided through a dermatological questionnaire (block 1120) and answers to the questionnaire may be obtained from the user (block 1130). For example, questionnaire analyzer 730 may provide a questionnaire that may ask the user to describe the skin condition by specifying which regions of the body are affected; by specifying a color, size, shape, texture, and/or distribution of the lesions; by selecting qualifying adjectives for the lesions, such as whether the lesions are dry, wet, oozing, scaly, fluid-filled, itchy, burning, etc.; and/or by selecting other descriptions applicable to the user's skin condition. Furthermore, the user may be asked to select applicable signs and symptoms, select known allergies, select medications that the user is taking, select that the user has eaten, select any pre-existing medical conditions that the user may have, select any events that may have contributed to the user's skin conditions, and/or select any other options that may be provided to the user in a questionnaire. The user may provide the answers by selecting a selectable object on a touch screen using a finger or a stylus, by using a keypad or a keyboard, using speech input, and/or by using another input mechanism associated with user device 110.

Context information associated with the user may be obtained (block 1140). For example, context analyzer 740 may determine a location associated with user device 110 and may determine any context information associated with the location. For example, context analyzer 740 may determine a current weather and/or recent weather history associated with the location (e.g., by obtaining the information from a weather service server device) and/or may search the interact for information associated with location using particular keywords or phrases (e.g., keywords indicative of an industrial accident, infection outbreak, etc.).

Features may be extracted from the obtained one or more images, from the questionnaire answers, and/or from the obtained context information (block 1150). For example, image analyzer 720 may perform feature extraction on the obtained one or more images, questionnaire analyzer 730 may convert the obtained answers into features, and context analyzer 740 may convert the obtained context information into features. The extracted features may be combined into a feature vector and provided to condition classifier 760. A dermatological analysis model may be applied to the obtained one or more images, questionnaire answers, and context information (block 1160). For example, condition classifier 760 may access the model stored in conditions model database 765 and may classify the combined feature vector into a particular dermatological condition (e.g., a particular disease). In one implementation, the classification may be based directly on features obtained from the one or more images. In another implementation, the one or more images may be processed to detect areas corresponding to lesions and classification may be determined based on the lesions. A process of lesion classification is described below with reference to FIG. 12.

A classification based on the dermatological analysis model may be determined (block 1170), a recommendation based on the dermatological analysis model may be determined (block 1180), and the determined classification and recommendation may be provided to the user (block 1190). For example, condition classifier 760 may classify the feature vector into a particular dermatological classification and may obtain information about the dermatological classification, along with a recommendation, to user interface 710. User interface 710 may display the recommendation to the user. For example, if the user dermatological classification corresponds to hives, the user may be provided with information about hives, along with a recommendation about getting tested for allergies.

The dermatological classification may be provided with a confidence score that may indicate a measure of confidence that the dermatological classification is correct. The confidence score may be based, for example, on how closely a feature vector associated with the one or more images, questionnaire answers, and/or context information matches the determined dermatological classification.

Figure 12:
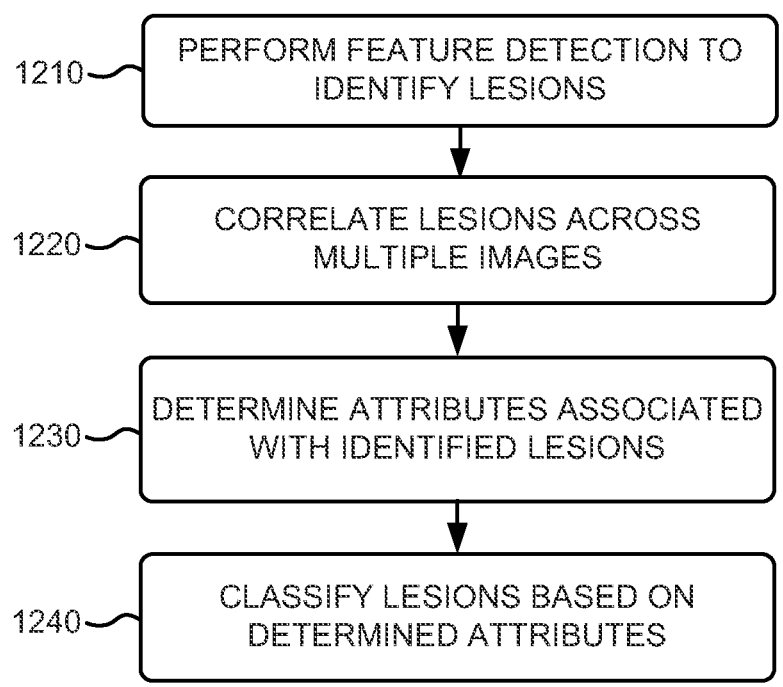
FIG. 12 is a flowchart of an exemplary process for classifying lesions according to an implementation described herein.

FIG. 12 is a flowchart of an exemplary process for classifying lesions according to an implementation described herein. For example, a dermatological classification may be determined more accurately if lesions associated with a skin conditions are classified first and if the dermatological classification is based on the classified lesions. In one implementation, the process of FIG. 12 may be performed by user device 110. In other implementations, some or all of the process of FIG. 12 may be performed by another device or a group of devices separate from user device 110 and/or including user device 110.

The process of FIG. 12 may include performing feature detection to identify lesions (block 1210). For example, image analyzer 720 may perform edge detection, block detection, template detection, or another type of detection to identify areas in an image that correspond to lesions. The lesions may be correlated across multiple images (block 1220). For example, image analyzer 720 may detect lesions for multiple images that were captured of a same area of skin and may tag the identified lesions in each image with a particular identifier.

Attributes associated with the lesions may be determined (block 1230). For example, lesion classifier 750 may convert particular features or sets of features, extracted by image analyzer 720, into particular attributes that may be associated with lesions. Examples of attributes that may be determined may include color of a lesion, shape of a lesion, size of a lesion, texture of a lesion, distribution of a group of lesions, and/or any other attribute that may be used to characterize a lesion.

The lesions may be classified based on the determined attributes (block 240). For example, lesion classifier 750 may access information stored in lesions model database 755 to classify an identified lesion into a lesion classification based on the attributes determined for the identified lesion. For example, a lesion may be classified as a macule, a papule, a nodule, a pustule, a tumor, a vesicle, a wheal, a scar, an erosion, a fissure, a crust, a scale, a lichenification, a furuncle, an excoriation, an ulceration, a keloid, an eschar, and/or as another type of lesion. Furthermore, a lesion may be further characterized as being annular, discrete, clustered, confluent, follicular, linear, reticular, serpiginous, morbilliform, and/or as being characterized by another type of modifying description.

Figure 13:
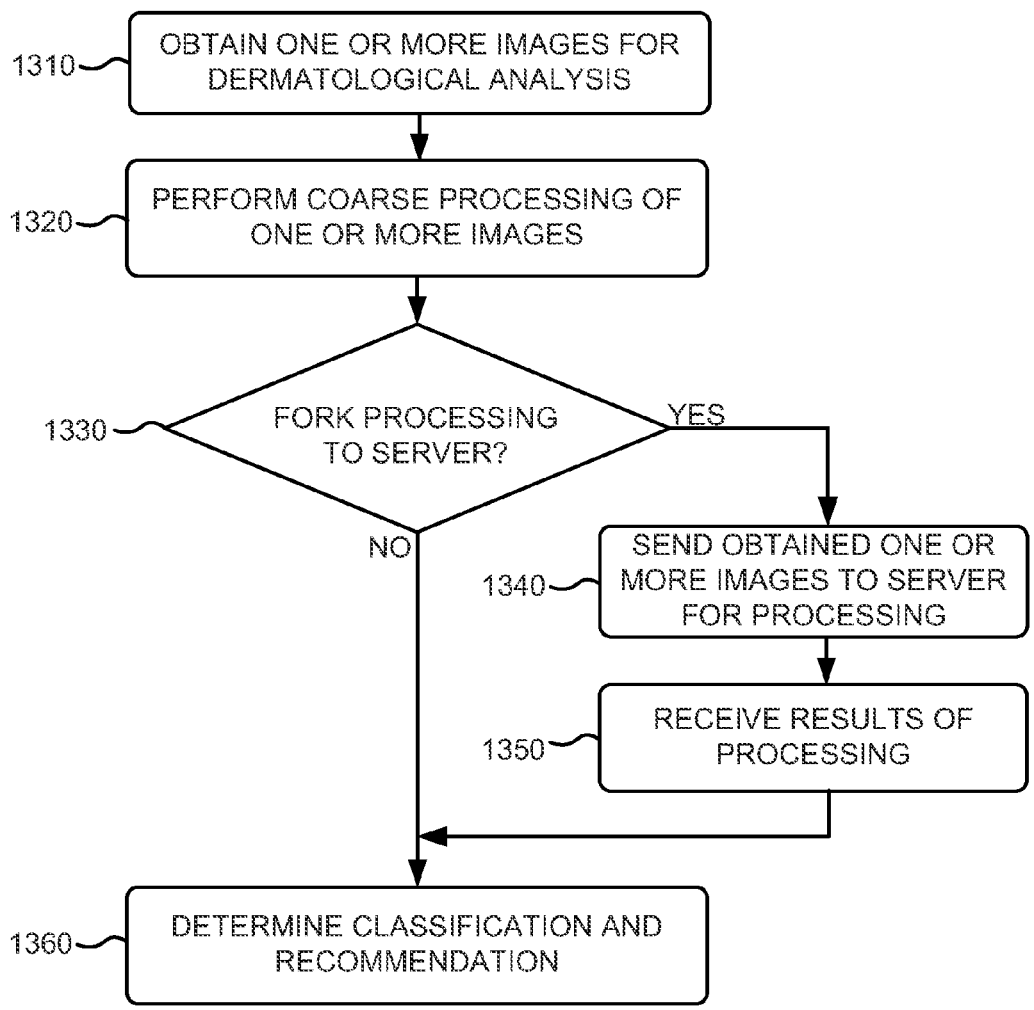
FIG. 13 is a flowchart of an exemplary process for processing information to generate a dermatological analysis and recommendation according to an implementation described herein.

FIG. 13 is a flowchart of an exemplary process for processing information to generate a dermatological analysis and recommendation according to an implementation described herein. In one implementation, the process of FIG. 13 may be performed by user device 110. In other implementations, some or all of the process of FIG. 13 may be performed by another device or a group of devices separate from user device 110 and/or including user device 110.

The process of FIG. 13 may include obtaining one or more images for dermatological analysis (block 1310). For example, one or more images may be obtained using the process of FIG. 10 described above. Coarse processing of the one or more images may be performed (block 1320). For example, image analyzer 720 may apply a first set of feature extraction techniques to the obtained one or more images, such as edge detection to identify lesions.

A determination may be made as to whether to fork processing to a server (block 1330). For example, image analyzer 720 may determine whether to send the obtained one or more images to dermatological analysis system 130 to perform further feature extraction on the obtained one or more images. Image analyzer 720 may make the determination based on one or more criteria.

For example, image analyzer 720 may make the determination based on a privacy setting associated with user device 110. If user device 110 is associated with a high privacy setting, the one or more images may not be sent to dermatological analysis system 130 and image processing may be performed locally by user device 110.

As another example, image analyzer 720 may make the determination based on the availability of computing resources and/or memory on user device 110. For example, if user device 110 is low on memory, image analyzer 720 may send the one or more images for processing to dermatological analysis system 130.

As yet another example, image analyzer 720 may make the determination based on a wireless connection to network 120. For example, if the wireless connection is associated with high noise or a low bandwidth, the one or more images may not be sent to dermatological analysis system 130 and all image processing may be performed locally by user device 110.

If it is determined that processing is to be forked to the server (block 1330 YES), the obtained one or more images may be sent to the server for processing (block 1340) results of the processing may be received (block 1350). For example, server interface 770 may provide the obtained one or more images to dermatological analysis system 130. Dermatological analysis system 130 may perform feature extraction on the obtained one or more images and may return a feature vector to user device 110. The returned feature vector may be combined with a partial feature vector generated by image analyzer 720 into a feature vector for the obtained one or more images. Processing may continue to block 1360.

Returning to block 1330, if it is determined that processing it not to be forked to the server (block 1330—NO), processing may continue locally at user device 110 to determine a classification and recommendation (block 1360). For example, processing may continue as described above with reference to FIG. 11.

Figure 14A:
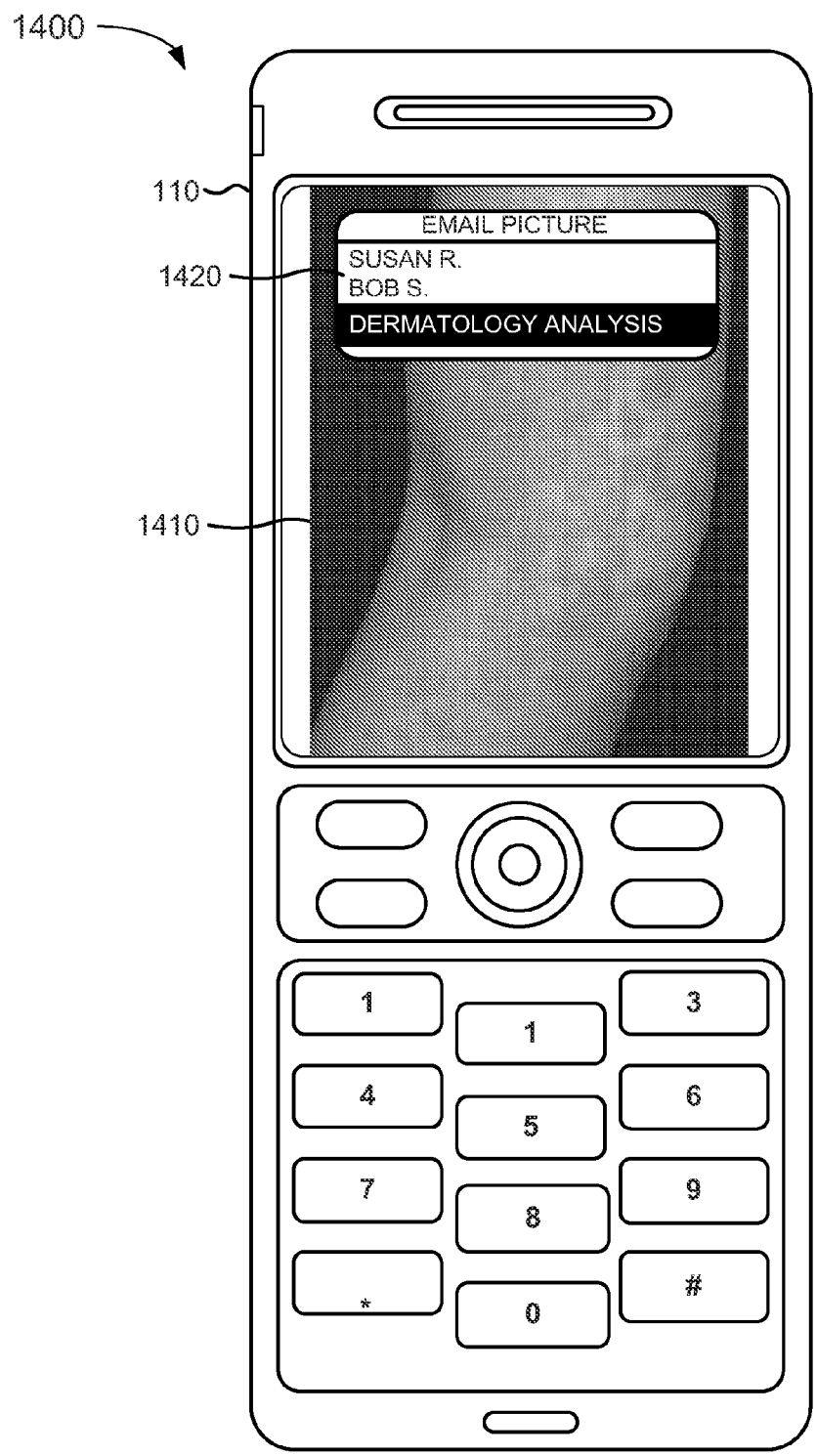
FIGS. 14A and 14B are diagrams of a first example that illustrates an implementation described herein.
Figure 14B:
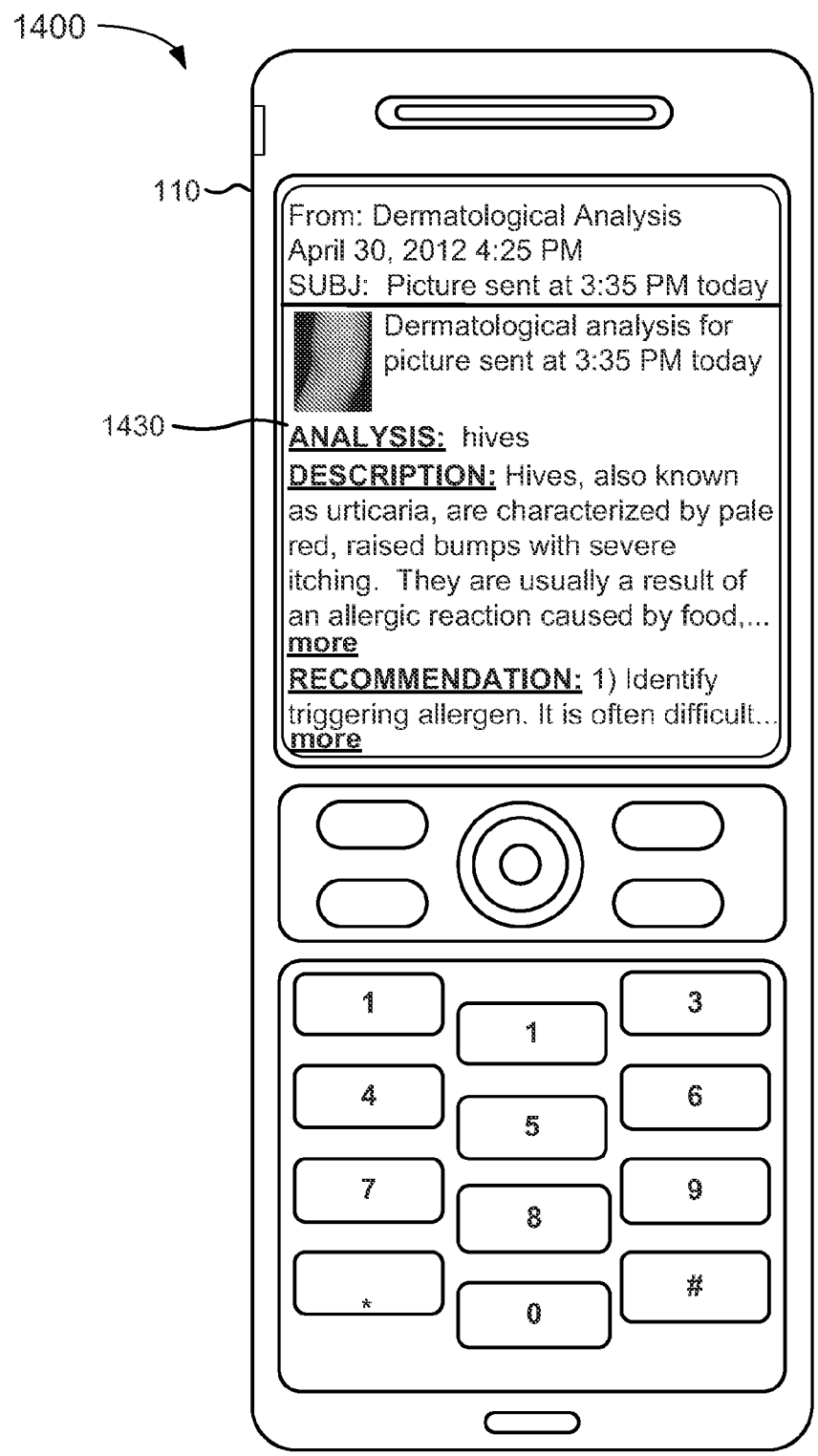

FIGS. 14A and 14B are diagrams of a first example 1400 that illustrates an implementation described herein. Example 1400 illustrates a dermatological analysis recommendation obtained using user device 110 of FIG. 2. User device 110 of FIG. 2 may not include dermatological analysis tool 701 and may not include different types of cameras or illumination devices to obtain detailed information about a user's skin condition. However, a user may capture an image 1410 and send the image to dermatological analysis system 130 along with a request for a dermatological analysis. For example, the user may select an address (e.g., an email address, a text messaging address, etc.) from a list of contacts 1420. FIG. 14B illustrates a response 1430 received by dermatological analysis system 130. For example, dermatological analysis system 130 may determine, based on image 1410, that the user has a skin condition known as hives and may provide a description of hives along with a recommendation.

Figure 15A:
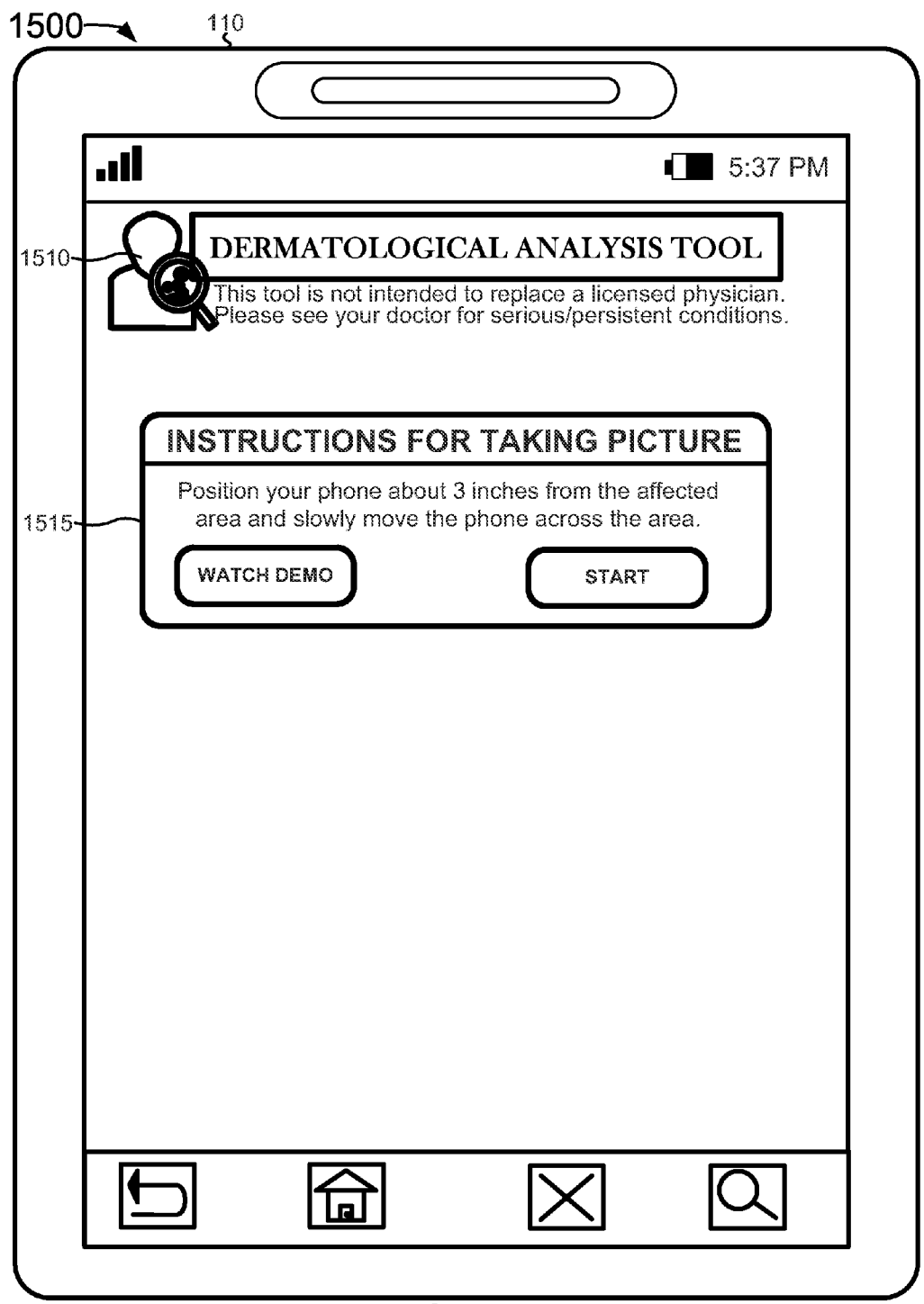
FIGS. 15A-15F are diagrams of a second example that illustrates an implementation described herein.

FIGS. 15A-15F are diagrams of a second example 1500 that illustrates an implementation described herein. Example 1500 illustrates operation of dermatological analysis tool 701. FIG. 15A illustrates a user interface 1510 associated with dermatological analysis tool 701. When dermatological analysis tool 701 is activated, a user may be provided with instructions 1515 for capturing an image.

Figure 15B:
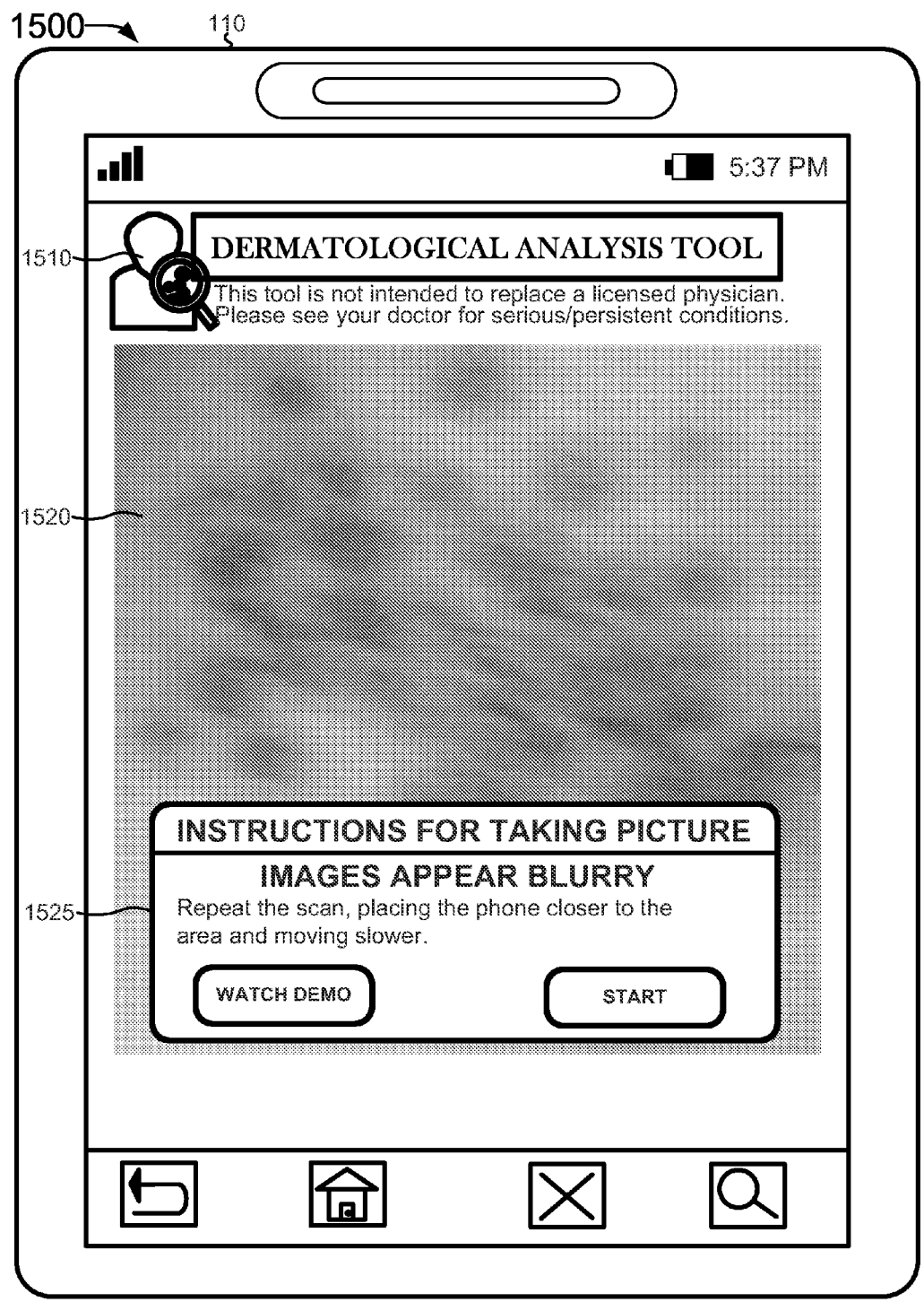

FIG. 15B illustrates a first image 1520 that the user captured. Image analyzer 720 may determine that the image is too blurry and may provide adjusted instructions 1525 to the user to repeat the capture process. The user may be guided through a process (not shown) that captures a first image at a high angle and a second image at a low angle. By capturing two images at different angles, the texture of lesions may be identified in more details than just by capturing a single image.

Figure 15C:
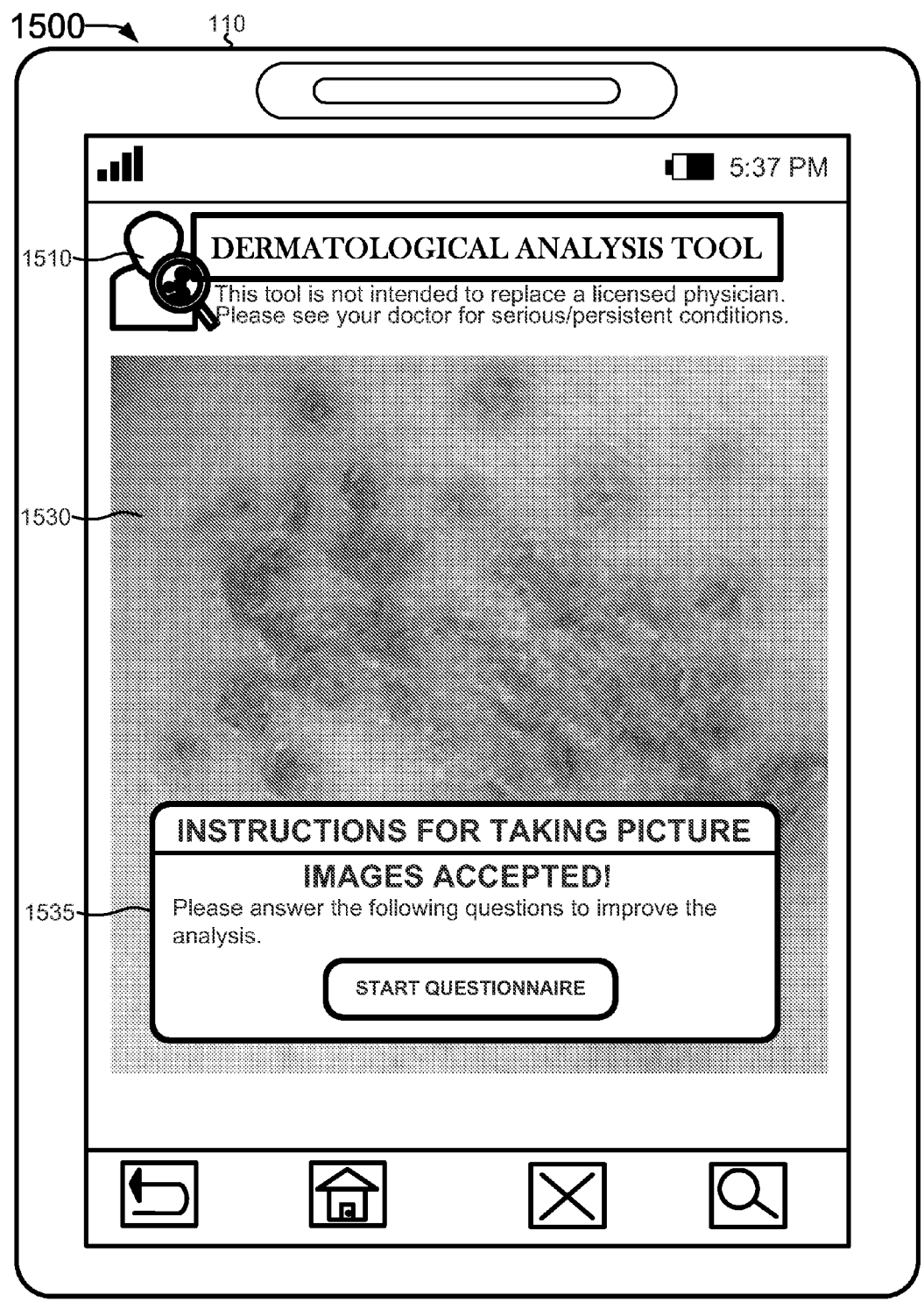
Figure 15D:
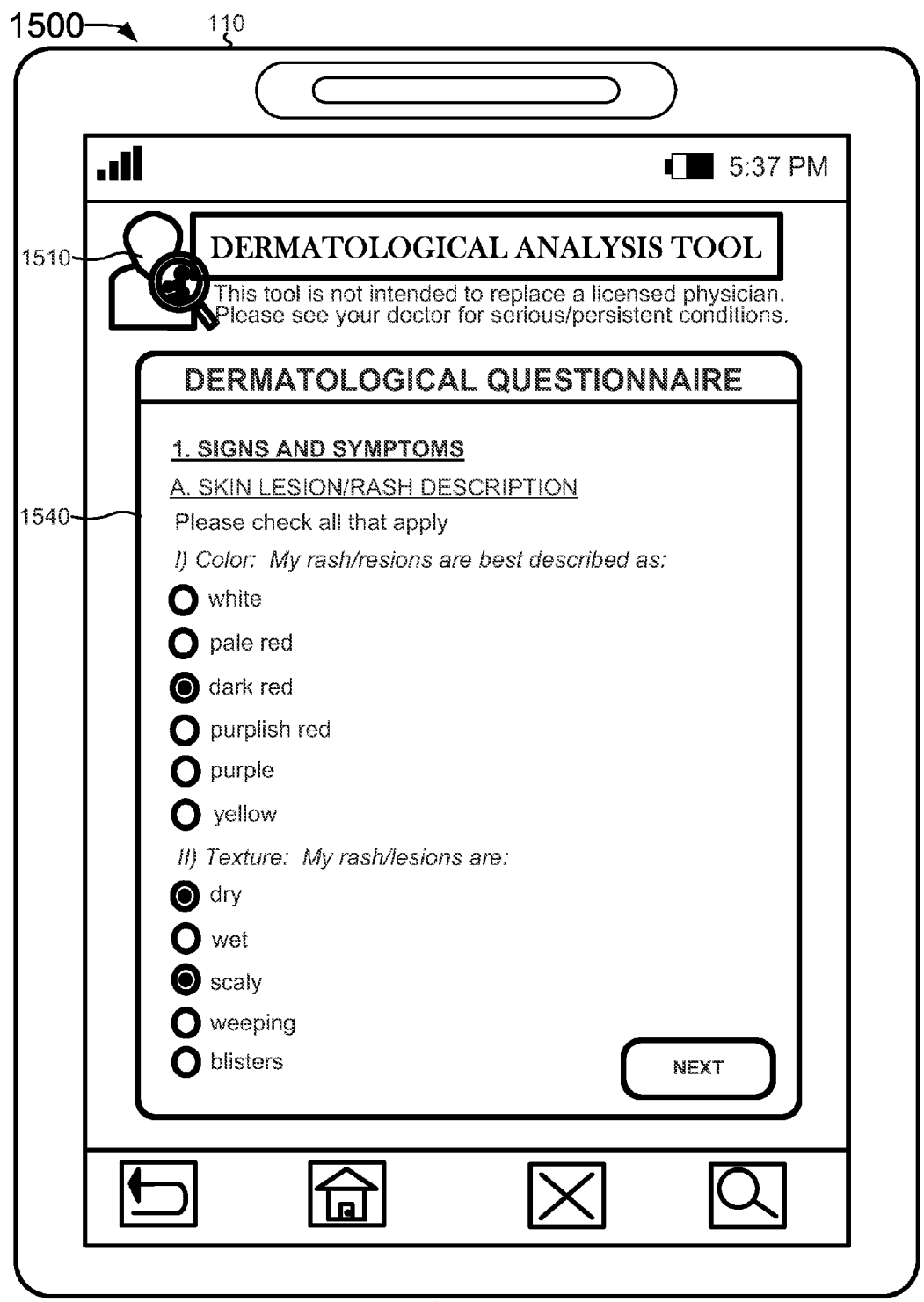

FIG. 15C illustrates a second image 1530 that may be accepted by image analyzer 720. The user may be provided with an indication 1535 that the images were accepted. FIG. 15D illustrates a questionnaire 1540 that may be provided to the user. The user may be prompted to provide answers to questions about the user's skin condition, questions about the user's signs and symptoms, etc. After the user has completed the questionnaire, the user's answers, along with the obtained images, may be analyzed to generate a feature vector.

Figure 15E:
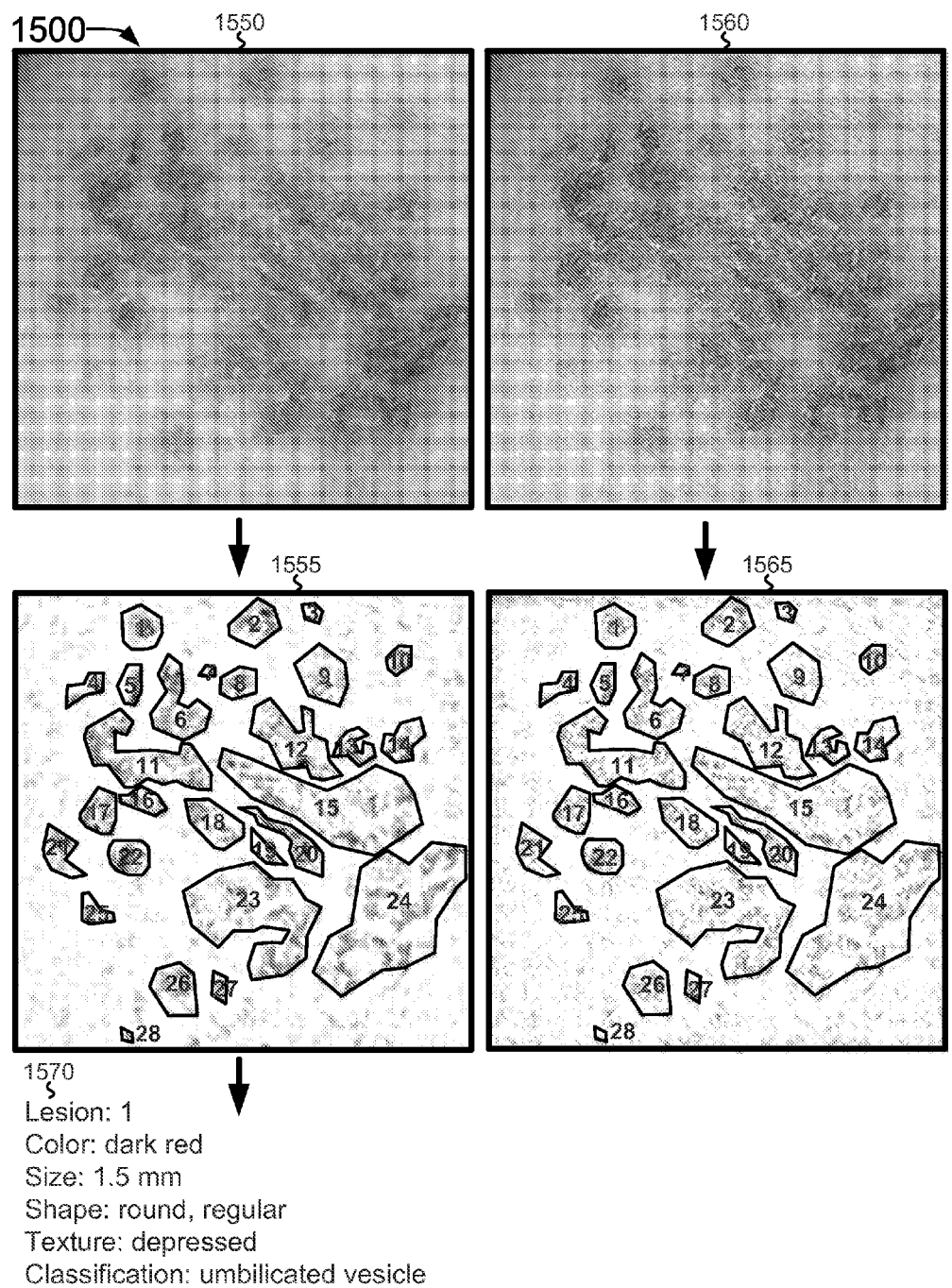

FIG. 15E illustrates a high angle image 1550 and a low angle image 1560 that may have been captured by the user. Feature detection may be performed to identify lesions. For example, first lesion map 1555 may include lesions detected in high angle image 1550 and second lesion map 1565 may include lesions detected in low angle image 1560. The lesions may be tagged and correlated across the two images.

Figure 15F:
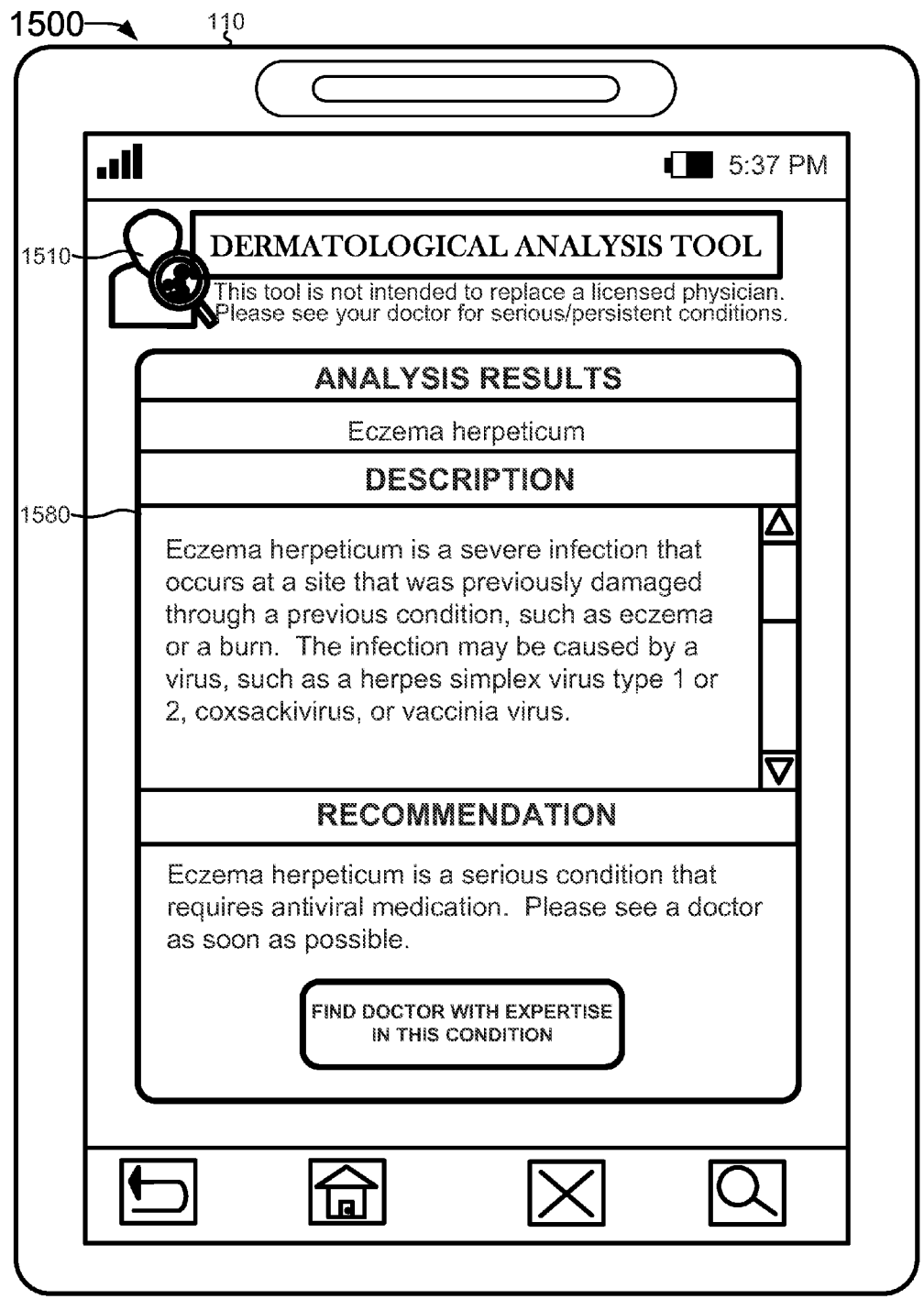

Feature extraction may be performed on each lesion and converted to a set of attributes 1570. The set of attributes may be used to classify the lesions. For example, the lesions in high angle image 1550 and low angle image 1560 may be classified as umbilicated vesicles. The classified lesions, along with the questionnaire answers, may be used to classify the dermatological condition associated with the user as eczema herpeticum. FIG. 15F illustrates user interface 1510 with the results 1580 of the dermatological analysis and a recommendation. For example, the recommendation may warn the user that the dermatological classification corresponds to a serious condition and may advise the user to see a physician.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while series of blocks have been described with respect to FIGS. 9-13, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in his specification are taken to specify the presence of stated features, integers, steps or components but does not preclude the presence or addition of one or more other features, integers, steps, components or groups thereof.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a mobile communication device, the method comprising:
    obtaining, by the mobile communication device, one or more images;
    extracting, by the mobile communication device, one or more features from the one or more images;
    generating, by the mobile communication device, a feature vector based on the extracted one or more features;
    determining, by the mobile communication device, a dermatological classification for the obtained one or more images based on the feature vector and based on a dermatological analysis model, wherein the dermatological analysis model is generated by:
        obtaining a set of images;
        obtaining one or more labels for a particular one of the obtained set of images;
        classifying the particular one of the obtained set of images into a particular dermatological classification based on the obtained one or more labels;
        extracting one or more features from the particular one of the obtained set of images; and associating the extracted one or more features with the particular dermatological classification;

determining, by the mobile communication device, a recommendation based on the determined dermatological classification; and providing, by the mobile communication device, information about the determined dermatological classification along with the recommendation to a user of the mobile communication device.

2. The method of claim 1, further comprising:

providing, via the mobile communication device, a dermatological questionnaire to the user in association with obtaining the one or more images;

receiving one or more answers to the dermatological questionnaire from the user; and wherein determining the dermatological classification for the obtained one or more images is further based on the received one or more answers to the dermatological questionnaire.

3. The method of claim 1, further comprising:

obtaining context information associated with the obtained one or more images, wherein the obtained context information includes one or more of:

weather information associated with the user's location, or an event associated with the user's location; and wherein determining the dermatological classification for the obtained one or more images is further based on the obtained context information.

4. The method of claim 1, wherein obtaining the one or more images includes:

receiving a request, from the user, to perform dermatological analysis;

providing one or more instructions to the user to capture the one or more images;

capturing the one or more images;

determining whether the captured one or more images satisfy one or more criteria;

determining one or more adjustments to the one or more instructions, when the captured one or more images do not satisfy the one or more criteria; and providing one or more adjusted instructions to the user, based on the determined one or more adjustments, when the captured one or more images do not satisfy the one or more criteria.

5. The method of claim 1, wherein the obtained one or more images include an infrared light image.

6. The method of claim 1, wherein the obtained one or more images include an ultraviolet light image.

7. The method of claim 1, wherein the obtained one or more images includes a polarized light image.

8. The method of claim 1, wherein the obtained one or more images include a first image taken at a first camera angle and a second image taken at a second camera angle, wherein the first camera angle is different from the second camera angle.

9. The method of claim 1, wherein the obtained one or more images include a first image taken at a first magnification and a second image taken at a second magnification, wherein the first magnification is different from the second magnification.

10. The method of claim 1, wherein the obtained one or more images include a first image taken at a first illumination intensity and a second image taken at a second illumination intensity, wherein the first illumination intensity is different from the second illumination intensity.

11. The method of claim 1, wherein extracting the one or more features from the one or more images includes:

identifying one or more lesions in the one or more images;

determining one or more attributes associated with the identified one or more lesions; and determining a classification for a particular one of the identified one or more lesions, wherein determining the dermatological classification for the obtained one or more images is based on the determined classification for the particular one of the identified one or more lesions.

12. The method of claim 11, wherein the determined one or more attributes include at least one of:

a color associated with the identified one or more lesions, a size associated with the identified one or more lesions, a shape associated with the identified one or more lesions, a texture associated with the identified one or more lesions, or a distribution associated with the identified one or more lesions.

13. The method of claim 1, wherein extracting the one or more features from the one or more images includes:

extracting a first set of features by the mobile communication device;

sending the obtained one or more images to a server device; and receiving a second set of features from the server device.

14. A mobile communication device comprising:

one or more memories; and one or more processors configured to:

obtain one or more images;

extract one or more features from the one or more images;

generate a feature vector based on the extracted one or more features;

determine a dermatological classification for the obtained one or more images based on the feature vector and based on a dermatological analysis model, wherein the dermatological analysis model is generated by:

obtaining a set of images;

obtaining one or more labels for a particular one of the obtained set of images;

classifying the particular one of the obtained set of images into a particular dermatological classification based on the obtained one or more labels;

extracting one or more features from the particular one of the obtained set of images; and associating the extracted one or more features with the particular dermatological classification;

determine a recommendation based on the determined dermatological classification; and provide information about the determined dermatological classification along with the recommendation to a user of the mobile communication device.

15. The mobile communication device of claim 14, wherein the mobile communication device includes a camera, wherein the one or more images are obtained using the camera, and wherein the camera includes at least one of:

an infrared light camera, an ultraviolet light camera, a polarized light camera, a macrophotography camera, or a dermatoscope.

16. The mobile communication device of claim 14, wherein the obtained one or more images include at least one of:

an infrared light image, an ultraviolet light image, a polarized light image, a first image taken at a first camera angle and a second image taken at a second camera angle, wherein the first camera angle is different from the second camera angle, a first image taken at a first magnification and a second image taken at a second magnification, wherein the first magnification is different from the second magnification, or a first image taken at a first illumination intensity and a second image taken at a second illumination intensity, wherein the first illumination intensity is different from the second illumination intensity.

17. The mobile communication device of claim 14, wherein the one or more processors are further configured to:
provide a dermatological questionnaire to the user in association with the obtained one or more images;
receive one or more answers to the dermatological questionnaire from the user; and
determine the dermatological classification for the obtained one or more images based on the received one or more answers to the dermatological questionnaire.

18. The mobile communication device of claim 14, wherein the one or more processors are further configured to:
identify one or more lesions in the one or more images;
determine one or more attributes associated with the identified one or more lesions, wherein the one or more attributes include at least one of:
a color associated with the identified one or more lesions,
a size associated with the identified one or more lesions,
a shape associated with the identified one or more lesions,
a texture associated with the identified one or more lesions, or
a distribution associated with the identified one or more lesions; determine a classification for a particular one of the identified one or more lesions; and
wherein the one or more processors are configured to determine the dermatological classification for the obtained one or more images based on the determined classification for the particular one of the identified one or more lesions.

19. A non-transitory computer-readable medium storing instructions executable by one or more processors, the non-transitory computer-readable medium comprising:
one or more instructions to obtain one or more images;
one or more instructions to extract one or more features from the obtained one or more images;
one or more instructions to provide a dermatological questionnaire to the user in association with the obtained one or more images;
one or more instructions to receive one or more answers to the dermatological questionnaire from the user;
one or more instructions to generate a feature vector based on the extracted one or more features and the received one or more answers;
one or more instructions to determine a dermatological classification for the obtained one or more images based on the feature vector and based on a dermatological analysis model,
wherein the dermatological analysis model is generated by:
obtaining a set of images;
obtaining one or more labels for a particular one of the obtained set of images;
classifying the particular one of the obtained set of images into a particular dermatological classification based on the obtained one or more labels;
extracting one or more features from the particular one of the obtained set of images; and
associating the extracted one or more features with the particular dermatological classification;
one or more instructions to determine a recommendation based on the determined dermatological classification; and
one or more instructions to provide information about the determined dermatological classification along with the recommendation to a user of the mobile communication device.

20. The non-transitory computer-readable medium of claim 19, wherein the obtained one or more images include a first image taken at a first camera angle and a second image taken at a second camera angle, wherein the first camera angle is different from the second camera angle.

* * * * *